(12) United States Patent
Streeper et al.

(10) Patent No.: US 8,541,183 B2
(45) Date of Patent: Sep. 24, 2013

(54) METHODS OF IDENTIFICATION, ASSESSMENT, PREVENTION AND THERAPY OF LUNG DISEASES AND KITS THEREOF

(75) Inventors: Robert T. Streeper, San Antonio, TX (US); Elzbieta Izbicka, San Antonio, TX (US); Sung H. Baek, Snohomish, WA (US)

(73) Assignee: Cancer Prevention and Cure, Ltd., Michigan City, IN (US)

( * ) Notice: Subject to any disclaimer, the term of this patent is extended or adjusted under 35 U.S.C. 154(b) by 893 days.

(21) Appl. No.: 12/403,369

(22) Filed: Mar. 12, 2009

(65) Prior Publication Data

US 2010/0009386 A1    Jan. 14, 2010

Related U.S. Application Data

(63) Continuation-in-part of application No. 12/208,437, filed on Sep. 11, 2008, now Pat. No. 7,888,051, and a continuation-in-part of application No. 12/208,876, filed on Sep. 11, 2008.

(60) Provisional application No. 60/971,440, filed on Sep. 11, 2007, provisional application No. 60/971,422, filed on Sep. 11, 2007.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/520; 530/300; 530/350

(58) Field of Classification Search
None
See application file for complete search history.

(56) References Cited

U.S. PATENT DOCUMENTS

| 2003/0104499 A1 | 6/2003 | Pressman et al. |
| 2003/0190602 A1 | 10/2003 | Pressman et al. |
| 2006/0084126 A1 | 4/2006 | Segal |

FOREIGN PATENT DOCUMENTS

| WO | WO 02-073204 | 9/2002 |
| WO | WO 2006-045318 | 5/2006 |
| WO | WO 2007-013671 | 2/2007 |
| WO | WO 2008/063413 | 5/2008 |

OTHER PUBLICATIONS

Iizasa et al. (Clinical Cancer Research, 1999, vol. 5,No. 1 pp. 149-153).*
Mattos et al. (Chest, 2002, vol. 122, pp. 1543-1552).*
Ma et al., "Alteration in Gene Expression Profile and Biological Behavior in Human Lung Cancer Cell Line NL9980 by nm23-H1 Gene Silencing," Biochemical and Biophysical Research Communications, vol. 371, No. 3, pp. 425-430 (2008).
International Search Report for International Application No. PCT/US2010/027243 mailed Jan. 7, 2011.
Written Opinion for International Application No. PCT/US2010/027243 mailed Jan. 7, 2011.
European Search Report from EP 10 75 1519 dated Dec. 6, 2012.
Wills-Karp, Marsha et al.; "Interleukin-13 in Asthma;" Pulmonary Medicine, vol. 9, pp. 21-27; 2003; XP009139299, ISSN 1070-5287.
Izuhara, K. et al.; "IL-13: A Promising Therapeutic Target for Bronchial Asthma;" Current Medicinal Chemistry, vol. 13, pp. 2291-2298; 2006; ISSN 0929-8673.
Bosse et al. "Serum Matrix Metalloproteinase-9: Tissueinhibitor of Metalloproteinase-1 Ratio Correlates with Steroid Responsiveness in Moderate to Severe Asthma," American Journal of Respiratory and Critical Care Medicine, 159: 596-602, 1999.
Camilla et al. "Flow Cytometric Microsphere-Based Immunoassay: Analysis of Secreted Cytokines in Whole-Blood Samples from Asthmatics," Luminex Publications—Journal: Clinical and Diagnostic Laboratory Immunology, pp. 776-784 (Abstract), 2001.
Koizumi et al. "Elevation of Serum Soluble Vascular Cell Adhesion Molecule-1 (sVCAM-1) Levels in Bronchial Asthma," Clinical and Experimental Immunology, 101:468-473 (Apr. 1995).
Huang et al. "Human Non-Small Cell Lung Cancer Cells Express a Type 2 Cytokine Pattern," Cancer Research, 55:3847-3853 (Sep. 2005).
Iizasa "Elevated Levels of Circulating Plasma Matrix Metalloproteinase 9 in Non-Small Cell Lung Cancer Patients," Clinical Cancer Research, 5(1): 149-153 (Jan. 1999).
Liu et al. "Multiplexed Analysis of Biomarkers Related to Obesity and the Metabolic Syndrome in Human Plasma, Using the Luminex-100 System," Clinical Chemistry 51(7):1 102-1109 (Jul. 2005).
Leonardi et al. "Matrix Metalloproteases in Vernal Keratoconjunctivitis, Nasal Polyps and Allergic Asthma," Clinical and Experimental Allergy, 37(6): pp. 872-879 (Abstract) (Jun. 2007).
Koomen et al. "Diagnostic Protein Discovery Using Proteolytic Peptide Targeting and Identification," Rapid Communications in Mass Spectrometry, 18(21): 2537-2548 (Nov. 2004).
Oh et al. "A Database of Protein Expression in Lung Cancer," Proteomics, 1(10): 1303-1319 (Oct. 2001).
Yanagisawa et al. "Proteomic Patterns of Tumor Subsets in Non-Small-Cell Lung Cancer," The Lancet, 362: pp. 433-439 (Aug. 2003).
Yeo et al. "Quantitative Profiling of Plasma Peptides in Asthmatic Mice Using Liquid Chromatography and Mass Spectrometry," Proteomics, 4(11): 3308-3317 (Nov. 2004).
International Search Report and the Written Opinion of the International Searching Authority, dated Nov. 19, 2008, issued in International Application No. PCT/U508/75953.
International Search Report, dated Dec. 11, 2008, issued in International Application No. PCT/U508/76049.

* cited by examiner

*Primary Examiner* — Lisa Cook
(74) *Attorney, Agent, or Firm* — Hunton & Williams LLP

(57) ABSTRACT

The invention provides biomarkers and combinations of biomarkers that are useful in diagnosing lung diseases such as non-small cell lung cancer or reactive airway disease. The invention also provides methods of differentiating lung disease, methods of monitoring therapy, and methods of predicting a subject's response to therapeutic intervention based on the extent of expression of the biomarkers and combinations of biomarkers. Kits comprising agents for detecting the biomarkers and combination of biomarkers are also provided.

28 Claims, 10 Drawing Sheets

FIGURE 1A

| | FLUORESCENCE INTENSITY LEVEL IN THE NORMAL POPULATION | | | | Biomarker | Ave | S.D. | R.S.D. |
|---|---|---|---|---|---|---|---|---|
| Biomarker | Ave | S.D. | R.S.D. | | MMP-3 | 15660.06 | 5918.30 | 37.79 |
| sE-Selectin | -3754.00 | 35.15 | -0.94 | | IP-10 | 3408.61 | 4279.11 | 125.54 |
| EGF | 5015.80 | 4447.17 | 88.66 | | IL-10 | 401.93 | 816.03 | 203.03 |
| IL-5 | -293.76 | 1201.87 | -409.13 | | MMP-8 | 2673.57 | 1392.34 | 52.08 |
| PAI-1 (total) | 4650.05 | 1273.31 | 27.38 | | MMP-2 | 24052.74 | 928.10 | 3.86 |
| Resistin | 3138.02 | 2234.38 | 71.20 | | G-CSF | -17.85 | 1164.65 | -6525.86 |
| Leptin | 8089.08 | 9137.49 | 112.96 | | sFasL | 59.40 | 29.11 | 49.00 |
| sVCAM-1 | 1017.74 | 609.37 | 59.87 | | IL-8 | 7726.40 | 6653.62 | 86.12 |
| MMP-13 | 0.30 | 6.35 | 2141.82 | | TGF-ALPHA | 2521.01 | 2820.52 | 111.88 |
| SAA | 1541.92 | 4224.24 | 273.96 | | IFN-gamma | 347.30 | 1150.62 | 331.31 |
| sICAM-1 | -3488.15 | 1784.70 | -51.16 | | MPO | 1960.51 | 4609.11 | 235.10 |
| CD40 Ligand | 161.20 | 192.05 | 119.14 | | MIP-1alpha | 2579.96 | 3201.87 | 124.11 |
| IL-7 | -553.29 | 2222.61 | -401.71 | | IL-1ra | 828.88 | 1771.02 | 213.66 |
| C-Peptide | 8734.89 | 8388.22 | 96.03 | | VEGF | 4791.40 | 5321.58 | 111.07 |
| HGF | 650.01 | 413.44 | 63.61 | | IL-13 | 664.75 | 2013.87 | 302.95 |
| CRP | 10243.98 | 8699.54 | 84.92 | | Insulin | 1485.90 | 3380.72 | 227.52 |
| IL-1alpha | 6574.13 | 9870.69 | 150.14 | | IL-12(p70) | 1174.46 | 4080.10 | 347.40 |
| MMP-7 | 309.12 | 88.76 | 28.71 | | IL-1B | 778.53 | 2976.43 | 382.32 |
| IL-4 | 2261.07 | 2731.85 | 120.82 | | GLP-1 (Active) | 708.76 | 2492.64 | 351.69 |
| Adiponectin | 24525.83 | 1290.90 | 5.26 | | FRACTALKINE | 916.75 | 2024.48 | 220.83 |
| MMP-9 | 28540.58 | 803.64 | 2.82 | | IL-2 | 534.85 | 1262.10 | 235.97 |
| GM-CSF | 103.94 | 973.06 | 936.21 | | EOTAXIN | 6342.86 | 6613.72 | 104.27 |
| MMP-12 | -2.29 | 2.48 | -108.31 | | MIP-1beta | 1513.50 | 3551.71 | 234.67 |
| IL-15 | 231.98 | 679.37 | 292.85 | | sFas | 181.43 | 63.29 | 34.88 |
| IL-17 | 1680.73 | 4225.28 | 251.40 | | Amylin (Active) | 1447.02 | 4589.31 | 317.16 |
| IL-12(p40), free | 171.55 | 1091.36 | 636.16 | | MMP-1 | 6010.22 | 4006.18 | 66.66 |
| MIF | 97.55 | 71.64 | 73.44 | | Glucagon | 1869.83 | 4635.13 | 247.89 |
| TNF-alpha | 1185.89 | 3586.20 | 302.41 | | MCP-1 | 27869.05 | 965.91 | 3.47 |
| I-TAC | 19.16 | 34.72 | 181.17 | | SAP | 24732.42 | 803.37 | 3.25 |
| IL-6 | 3557.94 | 5666.10 | 159.25 | | | | | |

FIGURE 1B

| FLUORESCENCE INTENSITY LEVEL IN THE LUNG CANCER POPULATION | | | | | | | |
|---|---|---|---|---|---|---|---|
| Biomarker | Ave | S.D. | R.S.D. | Biomarker | Ave | S.D. | R.S.D. |
| sE-Selectin | -3710.76 | 26.27 | -0.71 | MMP-3 | 15470.68 | 5795.86 | 37.46 |
| EGF | 12471.39 | 9397.19 | 75.35 | IP-10 | 5641.16 | 6148.52 | 108.99 |
| IL-5 | -947.96 | 859.85 | -90.70 | IL-10 | 1053.38 | 2430.64 | 230.75 |
| PAI-1 (total) | 3776.85 | 1098.08 | 29.07 | MMP-8 | 2845.20 | 1305.16 | 45.87 |
| Resistin | 2084.83 | 853.26 | 40.93 | MMP-2 | 23768.35 | 1272.05 | 5.35 |
| Leptin | 24.05 | 8538.62 | 35503.61 | G-CSF | -209.22 | 896.64 | -428.57 |
| sVCAM-1 | 1364.62 | 912.59 | 66.88 | sFasL | 487.48 | 2434.79 | 499.46 |
| MMP-13 | -1.10 | 3.81 | -345.47 | IL-8 | 7258.97 | 8912.30 | 122.78 |
| SAA | 7712.92 | 10706.73 | 138.82 | TGF-ALPHA | 1859.04 | 4739.54 | 254.95 |
| sICAM-1 | -2484.13 | 3305.66 | -133.07 | IFN-gamma | 248.91 | 1141.12 | 458.45 |
| CD40 Ligand | 539.63 | 495.14 | 91.76 | MPO | 2899.33 | 5179.23 | 178.64 |
| IL-7 | -1723.03 | 869.90 | -50.49 | MIP-1alpha | 4869.60 | 7669.88 | 157.51 |
| C-Peptide | 10380.92 | 8201.68 | 79.01 | IL-1ra | 298.27 | 535.27 | 179.46 |
| HGF | 560.93 | 421.36 | 75.12 | VEGF | 7222.50 | 6074.27 | 84.10 |
| CRP | 20810.52 | 6683.21 | 32.11 | IL-13 | 373.67 | 713.36 | 190.90 |
| IL-1alpha | 404.89 | 5992.97 | 1480.15 | Insulin | 1758.20 | 3177.46 | 180.72 |
| MMP-7 | 583.63 | 674.48 | 115.57 | IL-12(p70) | 208.66 | 701.87 | 336.37 |
| IL-4 | 422.10 | 1652.03 | 391.38 | IL-1B | 1278.97 | 3946.61 | 308.58 |
| Adiponectin | 24462.63 | 1616.93 | 6.61 | GLP-1 (Active) | 229.15 | 437.88 | 191.09 |
| MMP-9 | 27269.90 | 1233.41 | 4.52 | FRACTALKINE | 279.20 | 747.82 | 267.85 |
| GM-CSF | -188.48 | 771.98 | -409.58 | IL-2 | 178.31 | 421.41 | 236.34 |
| MMP-12 | -0.65 | 2.25 | -345.94 | EOTAXIN | 6982.76 | 6113.93 | 87.56 |
| IL-15 | 19.63 | 139.23 | 709.13 | MIP-1beta | 924.40 | 2438.49 | 263.79 |
| IL-17 | 265.67 | 812.81 | 305.94 | sFas | 214.14 | 140.95 | 65.82 |
| IL-12(p40), free | -115.91 | 847.03 | -730.77 | Amylin (Active) | 889.30 | 1721.49 | 193.58 |
| MIF | 331.60 | 1019.01 | 307.30 | MMP-1 | 7517.19 | 6016.10 | 80.03 |
| TNF-alpha | 379.20 | 644.19 | 169.88 | Glucagon | 2319.96 | 3302.68 | 142.36 |
| I-TAC | 7.90 | 24.12 | 305.44 | MCP-1 | 27622.58 | 1394.00 | 5.05 |
| IL-6 | 1581.59 | 3261.99 | 206.25 | SAP | 24537.83 | 742.40 | 3.03 |

FIGURE 1C

| FLUORESCENCE INTENSITY LEVEL IN THE ASTHMA POPULATION |||||||
|---|---|---|---|---|---|---|
| Biomarker | Ave | S.D. | R.S.D. | Biomarker | Ave | S.D. | R.S.D. |
| sE-Selectin | 106.77 | 49.48 | 46.35 | MMP-3 | 12561.00 | 6374.02 | 50.74 |
| EGF | 1891.44 | 2231.32 | 117.97 | IP-10 | 2936.55 | 4067.24 | 138.50 |
| IL-5 | 1652.42 | 2751.18 | 166.49 | IL-10 | 230.17 | 601.55 | 261.35 |
| PAI-1 (total) | -2816.18 | 1591.94 | -56.53 | MMP-8 | 2134.40 | 1521.23 | 71.27 |
| Resistin | 1113.54 | 1337.70 | 120.13 | MMP-2 | 24772.42 | 2488.88 | 10.05 |
| Leptin | 17523.57 | 8823.12 | 50.35 | G-CSF | 164.26 | 1467.85 | 893.59 |
| sVCAM-1 | 3784.43 | 856.94 | 22.64 | sFasL | 49.41 | 80.27 | 162.46 |
| MMP-13 | 3.94 | 4.58 | 116.10 | IL-8 | 5297.59 | 6465.20 | 122.04 |
| SAA | 1415.16 | 1503.12 | 106.22 | TGF-ALPHA | 3565.40 | 4963.06 | 139.20 |
| sICAM-1 | 5039.72 | 2494.41 | 49.49 | IFN-gamma | 66.13 | 170.57 | 257.94 |
| CD40 Ligand | 703.27 | 459.33 | 65.31 | MPO | 2477.35 | 3110.70 | 125.57 |
| IL-7 | -634.33 | 1674.74 | -264.02 | MIP-1alpha | 3104.09 | 3288.61 | 105.94 |
| C-Peptide | 21354.00 | 5055.31 | 23.67 | IL-1ra | 573.51 | 893.00 | 155.71 |
| HGF | 904.47 | 455.18 | 50.33 | VEGF | 5570.03 | 4663.60 | 83.73 |
| CRP | 12052.08 | 8985.63 | 74.56 | IL-13 | 541.10 | 816.76 | 150.94 |
| IL-1alpha | 5722.73 | 9910.91 | 173.19 | Insulin | 2948.06 | 4584.49 | 155.51 |
| MMP-7 | 385.99 | 137.37 | 35.59 | IL-12(p70) | 444.58 | 651.36 | 146.51 |
| IL-4 | 2366.17 | 4127.72 | 174.45 | IL-1B | 166.73 | 367.22 | 220.25 |
| Adiponectin | 21241.91 | 3183.07 | 14.98 | GLP-1 (Active) | 273.07 | 539.24 | 197.47 |
| MMP-9 | 28559.72 | 916.63 | 3.21 | FRACTALKINE | 318.34 | 752.30 | 236.32 |
| GM-CSF | 574.11 | 1081.15 | 188.32 | IL-2 | 386.20 | 561.42 | 145.37 |
| MMP-12 | -0.88 | 3.26 | -372.85 | EOTAXIN | 6985.59 | 4047.59 | 57.94 |
| IL-15 | 193.73 | 294.67 | 152.10 | MIP--beta | 550.53 | 1038.97 | 188.72 |
| IL-17 | 1267.20 | 2096.39 | 165.44 | sFas | 238.89 | 184.67 | 77.30 |
| IL-12(p40), free | 361.39 | 899.35 | 248.86 | Amylin (Active) | 995.40 | 2621.90 | 263.40 |
| MIF | 143.50 | 79.27 | 55.24 | MMP-1 | 6968.82 | 5642.31 | 80.97 |
| TNF-alpha | 917.00 | 878.85 | 95.84 | Glucagon | 1598.53 | 3655.30 | 228.67 |
| I-TAC | 20.77 | 12.07 | 58.12 | MCP-1 | 27601.89 | 2359.19 | 8.55 |
| IL-6 | 4559.95 | 6199.94 | 135.97 | SAP | 24394.42 | 1810.34 | 7.42 |

FIGURE 1D

| | PERCENT CHANGE IN MEAN FLUORESCENCE INTENSITY | | | | | | |
|---|---|---|---|---|---|---|---|
| Biomarker | LC vs NO | AST vs NO | LC vs AST | Biomarker | LC vs NO | AST vs NO | LC vs AST |
| sE-Selectin | -1.15 | -102.84 | -3600.09 | MMP-3 | -1.21 | -19.79 | -51.45 |
| EGF | 148.64 | -62.29 | 1255.02 | IP-10 | 65.50 | -13.85 | 709.83 |
| IL-5 | 222.70 | -662.50 | -104.99 | IL-10 | 162.08 | -42.73 | -10.72 |
| PAI-1 (total) | -18.78 | -160.56 | -222.72 | MMP-8 | 6.42 | -20.17 | 122.89 |
| Resistin | -33.56 | -64.51 | 186.59 | MMP-2 | -1.18 | 2.99 | -7.54 |
| Leptin | -99.70 | 116.63 | -129.48 | G-CSF | 1072.30 | -1020.42 | 293.76 |
| sVCAM-1 | 34.08 | 271.85 | -65.45 | sFasL | 720.72 | -16.82 | -14.38 |
| MMP-13 | -471.91 | 1229.05 | -8.70 | IL-8 | -6.05 | -31.44 | 339.52 |
| SAA | 400.22 | -8.22 | 524.17 | TGF-ALPHA | -26.26 | 41.43 | 300.77 |
| sICAM-1 | -28.78 | -244.48 | -215.09 | IFN-gamma | -28.33 | -80.96 | 232.69 |
| CD40 Ligand | 234.76 | 336.27 | -60.21 | MPO | 47.89 | 26.36 | -218.24 |
| IL-7 | 211.41 | 14.65 | 70.89 | MIP-1alpha | 88.75 | 20.32 | 147.13 |
| C-Peptide | 18.84 | 144.47 | 58.39 | IL-1ra | 64.02 | 30.81 | 137.89 |
| HGF | -13.70 | 39.15 | -129.39 | VEGF | 50.74 | 16.25 | 115.00 |
| CRP | 103.15 | 17.65 | 117.23 | IL-13 | -43.79 | -18.60 | -101.85 |
| IL-1alpha | -93.84 | -12.95 | -27.14 | Insulin | 18.33 | 98.40 | -82.50 |
| MMP-7 | 88.80 | 24.87 | -27.90 | IL-12(p70) | -82.23 | -62.15 | -46.85 |
| IL-4 | -81.33 | 4.65 | -65.13 | IL-1B | 64.28 | -78.58 | 10.66 |
| Adiponectin | -0.26 | -13.39 | 12.60 | GLP-1 (Active) | -67.67 | -61.47 | 70.47 |
| MMP-9 | -4.45 | 0.07 | -3.87 | FRACTALKINE | -69.54 | -65.28 | -43.21 |
| GM-CSF | -281.34 | 452.37 | -140.55 | IL-2 | -66.66 | -27.79 | 14.84 |
| MMP-12 | -71.66 | -61.85 | -100.00 | EOTAXIN | 10.09 | 10.13 | -64.76 |
| IL-15 | -91.54 | -16.49 | -8.38 | MIP-1beta | -38.92 | -63.63 | 7.17 |
| IL-17 | -84.19 | -24.60 | -94.81 | sFas | 18.03 | 31.67 | -54.25 |
| IL-12(p40), free | -167.56 | 110.66 | -297.38 | Amylin (Active) | -38.54 | -31.21 | 18.55 |
| MIF | 239.94 | 47.11 | 267.31 | MMP-1 | 25.07 | 15.95 | -23.61 |
| TNF-alpha | -68.02 | -22.67 | -7.11 | Glucagon | 24.07 | -14.51 | -24.79 |
| I-TAC | -58.79 | 8.37 | -38.37 | MCP-1 | -0.88 | -0.96 | -0.24 |
| IL-6 | -55.55 | 28.16 | -54.85 | SAP | -0.79 | -1.37 | -2.51 |

FIGURE 1E

| SIGNIFICANCE OF POPULATION DIFFERENCES EXPRESSED AS PROBABILITY OF STUDENT'S T VALUE ||||||||
|---|---|---|---|---|---|---|---|
| Biomarker | LC vs NO | AST vs NO | LC vs AST | Biomarker | LC vs NO | AST vs NO | LC vs AST |
| sE-Selectin | 0.000 | 0.000 | 0.000 | MMP-3 | 0.901 | | |
| EGF | 0.000 | 0.001 | 0.000 | IP-10 | 0.108 | 0.669 | |
| IL-5 | 0.018 | 0.001 | 0.000 | IL-10 | 0.169 | 0.368 | |
| PAI-1 (total) | 0.006 | 0.000 | 0.000 | MMP-8 | 0.624 | 0.164 | |
| Resistin | 0.019 | 0.000 | 0.002 | MMP-2 | 0.327 | 0.145 | |
| Leptin | 0.001 | 0.000 | 0.000 | G-CSF | 0.479 | 0.602 | 0.244 |
| sVCAM-1 | | 0.000 | 0.000 | sFasL | 0.340 | 0.526 | 0.346 |
| MMP-13 | 0.305 | 0.016 | 0.000 | IL-8 | 0.819 | 0.165 | 0.344 |
| SAA | 0.005 | 0.881 | 0.003 | TGF-ALPHA | 0.514 | 0.325 | 0.186 |
| sICAM-1 | 0.149 | 0.000 | 0.000 | IFN-gamma | 0.741 | 0.206 | 0.405 |
| CD40 Ligand | 0.000 | 0.000 | 0.198 | MPO | 0.461 | 0.621 | 0.711 |
| IL-7 | 0.009 | 0.877 | 0.003 | MIP-1alpha | 0.137 | 0.541 | 0.265 |
| C-Peptide | 0.467 | 0.000 | 0.000 | IL-1ra | 0.122 | 0.496 | 0.157 |
| HGF | 0.412 | 0.030 | 0.004 | VEGF | 0.105 | 0.557 | 0.253 |
| CRP | 0.000 | 0.440 | 0.000 | IL-13 | 0.459 | 0.764 | 0.408 |
| IL-1alpha | 0.005 | 0.744 | 0.016 | Insulin | 0.761 | 0.170 | 0.283 |
| MMP-7 | 0.031 | 0.014 | 0.134 | IL-12(p70) | 0.206 | 0.354 | 0.191 |
| IL-4 | 0.003 | 0.909 | 0.021 | IL-1B | 0.581 | 0.285 | 0.143 |
| Adiponectin | 0.868 | 0.000 | 0.000 | GLP-1 (Active) | 0.357 | 0.369 | 0.751 |
| MMP-9 | 0.000 | 0.933 | 0.000 | FRACTALKINE | 0.111 | 0.147 | 0.843 |
| GM-CSF | 0.202 | | 0.003 | IL-2 | 0.148 | 0.569 | 0.115 |
| MMP-12 | 0.009 | | 0.760 | EOTAXIN | 0.699 | 0.660 | 0.998 |
| IL-15 | | 0.785 | 0.005 | MIP-1beta | 0.457 | 0.173 | 0.456 |
| IL-17 | | 0.642 | 0.018 | sFas | 0.251 | 0.114 | 0.567 |
| IL-12(p40), free | 0.259 | 0.475 | 0.042 | Amylin (Active) | 0.575 | 0.650 | 0.866 |
| MIF | 0.215 | 0.024 | 0.335 | MMP-1 | 0.258 | 0.456 | 0.722 |
| TNF-alpha | 0.230 | 0.701 | 0.010 | Glucagon | 0.690 | 0.806 | 0.462 |
| I-TAC | 0.150 | 0.818 | 0.014 | MCP-1 | 0.429 | 0.570 | 0.967 |
| IL-6 | 0.103 | 0.523 | 0.025 | SAP | 0.334 | 0.357 | 0.691 |

FIGURE 2A

| \multicolumn{4}{c}{FLUORESCENCE INTENSITY LEVEL IN THE NORMAL POPULATION} |
|---|---|---|---|
| Biomarker | Ave | S.D. | R.S.D. |
| Adiponectin | 2339.70 | 1601.88 | 68.46 |
| Resistin | 114.63 | 91.26 | 79.61 |
| PAI-1 | 366.00 | 424.13 | 115.88 |
| SE-selectin | 63.11 | 49.58 | 78.55 |
| sVCAM-1 | 1634.10 | 408.80 | 25.02 |
| sICAM-1 | 3541.68 | 1752.76 | 49.49 |
| MPO | 717.62 | 1645.83 | 229.35 |
| CRP | 8839.73 | 6391.84 | 72.31 |
| SAA | 1970.35 | 3668.84 | 186.20 |
| SAP | 2160.88 | 597.89 | 27.67 |
| Leptin | 2638.03 | 3025.87 | 114.70 |
| GLP-1 | 57.77 | 100.58 | 174.10 |
| Amylin (Total) | 120.65 | 256.04 | 212.21 |
| C-Peptide | 5015.95 | 2022.03 | 40.31 |
| Insulin | 322.77 | 436.71 | 135.30 |
| Sfas | 49.72 | 183.17 | 368.37 |
| sFSl | 13.17 | 12.32 | 93.54 |
| MIF | 61.95 | 113.33 | 182.95 |
| IL-1β | 23.50 | 11.80 | 50.24 |
| IL-2 | 13.13 | 55.39 | 421.85 |
| IL-1ra | 22.32 | 24.11 | 108.02 |
| IL-4 | 112.05 | 66.15 | 59.03 |
| IL-5 | 17.40 | 19.03 | 109.38 |
| IL-6 | 36.69 | 50.08 | 136.52 |
| IL-7 | 14.32 | 5.44 | 37.95 |
| TGF-α | 32.10 | 8.07 | 25.13 |
| Fractalkine | 12.69 | 3.15 | 24.80 |
| IL-8 | 280.43 | 703.76 | 250.96 |
| IL-10 | 12.55 | 3.87 | 30.82 |
| IL-15 | 24.21 | 4.43 | 18.28 |
| IL-17 | 36.44 | 13.75 | 37.74 |
| IL-1α | 83.74 | 148.45 | 177.27 |
| IFN-γ | 21.75 | 5.92 | 27.23 |
| G-CSF | 23.75 | 4.58 | 19.27 |
| GM-CSF | 27.98 | 14.45 | 51.65 |
| TNF-α | 39.67 | 17.41 | 43.88 |
| MCP-1 | 49.72 | 34.31 | 69.02 |
| IL-12 (p40), free | 24.17 | 7.86 | 32.54 |
| MIP-1α | 39.78 | 27.14 | 68.22 |
| MIP-1β | 20.27 | 9.77 | 48.19 |
| VEGF | 41.55 | 13.17 | 31.71 |

FIGURE 2B

| FLUORESCENCE INTENSITY LEVEL IN THE LUNG CANCER POPULATION | | | |
|---|---|---|---|
| Biomarker | Ave | S.D. | R.S.D. |
| Adiponectin | 2534.09 | 1827.31 | 72.11 |
| Resistin | 149.61 | 142.26 | 95.09 |
| PAI-1 | 629.60 | 307.11 | 48.78 |
| SE-selectin | 36.61 | 58.58 | 160.04 |
| sVCAM-1 | 1599.09 | 586.93 | 36.70 |
| sICAM-1 | 3079.69 | 1607.64 | 52.20 |
| MPO | 3000.57 | 2145.32 | 71.50 |
| CRP | 12563.08 | 6483.62 | 51.61 |
| SAA | 7173.28 | 7659.62 | 106.78 |
| SAP | 1161.51 | 897.26 | 77.25 |
| Leptin | 802.52 | 1210.97 | 150.90 |
| GLP-1 | 135.12 | 727.35 | 538.29 |
| Amylin (Total) | 301.16 | 1096.20 | 363.99 |
| C-Peptide | 2820.47 | 1931.78 | 68.49 |
| Insulin | 231.23 | 704.98 | 304.88 |
| Sfas | 42.69 | 32.34 | 75.77 |
| sFSl | 8.88 | 5.26 | 59.19 |
| MIF | 126.13 | 225.30 | 178.62 |
| IL-1β | 25.60 | 3.06 | 11.94 |
| IL-2 | 9.61 | 3.44 | 35.78 |
| IL-1ra | 26.67 | 6.50 | 24.39 |
| IL-4 | 90.91 | 45.70 | 50.27 |
| IL-5 | 14.17 | 4.90 | 34.60 |
| IL-6 | 56.88 | 201.09 | 353.57 |
| IL-7 | 27.30 | 115.37 | 422.52 |
| TGF-α | 32.23 | 8.82 | 27.38 |
| Fractalkine | 13.29 | 3.05 | 22.97 |
| IL-8 | 98.68 | 120.57 | 122.19 |
| IL-10 | 22.46 | 74.90 | 333.47 |
| IL-15 | 24.30 | 2.82 | 11.61 |
| IL-17 | 50.64 | 39.88 | 78.76 |
| IL-1α | 48.51 | 23.72 | 48.91 |
| IFN-γ | 23.99 | 6.93 | 28.87 |
| G-CSF | 24.96 | 16.23 | 65.03 |
| GM-CSF | 28.98 | 3.60 | 12.43 |
| TNF-α | 90.78 | 565.51 | 622.96 |
| MCP-1 | 149.53 | 230.71 | 154.29 |
| IL-12 (p40), free | 21.72 | 8.15 | 37.51 |
| MIP-1α | 63.94 | 150.25 | 235.00 |
| MIP-1β | 38.30 | 127.37 | 332.54 |
| VEGF | 40.73 | 22.15 | 54.38 |

FIGURE 2C

| FLUORESCENCE INTENSITY LEVEL IN THE LUNG CANCER POPULATION | | | |
|---|---|---|---|
| Biomarker | Ave | S.D. | R.S.D. |
| Adiponectin | 3035.92 | 2008.84 | 66.17 |
| Resistin | 265.24 | 189.24 | 71.35 |
| PAI-1 | 788.76 | 267.12 | 33.87 |
| SE-selectin | 38.80 | 30.29 | 78.07 |
| sVCAM-1 | 2988.12 | 948.06 | 31.73 |
| sICAM-1 | 3466.48 | 1326.54 | 38.27 |
| MPO | 4005.47 | 2572.12 | 64.22 |
| CRP | 10609.85 | 6186.73 | 58.31 |
| SAA | 3862.88 | 4256.70 | 110.19 |
| SAP | 2558.42 | 654.11 | 25.57 |
| Leptin | 2901.26 | 3238.21 | 111.61 |
| GLP-1 | 133.45 | 627.72 | 470.36 |
| Amylin (Total) | 347.48 | 1257.27 | 361.82 |
| C-Peptide | 5798.84 | 2767.02 | 47.72 |
| Insulin | 493.28 | 1468.20 | 297.64 |
| Sfas | 82.05 | 41.68 | 50.80 |
| sFSl | 33.56 | 50.68 | 151.01 |
| MIF | 69.89 | 48.66 | 69.62 |
| IL-1β | 41.58 | 151.82 | 365.11 |
| IL-2 | 12.75 | 3.63 | 28.46 |
| IL-1ra | 27.03 | 5.07 | 18.78 |
| IL-4 | 216.14 | 368.04 | 170.28 |
| IL-5 | 42.86 | 89.64 | 209.14 |
| IL-6 | 174.63 | 694.85 | 397.90 |
| IL-7 | 28.25 | 15.68 | 55.53 |
| TGF-α | 43.24 | 13.20 | 30.54 |
| Fractalkine | 16.13 | 3.54 | 21.96 |
| IL-8 | 1123.79 | 2876.50 | 255.96 |
| IL-10 | 15.80 | 3.81 | 24.10 |
| IL-15 | 30.22 | 8.18 | 27.08 |
| IL-17 | 57.59 | 27.56 | 47.86 |
| IL-1α | 294.98 | 854.12 | 289.55 |
| IFN-γ | 26.60 | 5.96 | 22.40 |
| G-CSF | 32.29 | 14.01 | 43.40 |
| GM-CSF | 40.62 | 33.59 | 82.70 |
| TNF-α | 88.03 | 350.87 | 398.57 |
| MCP-1 | 555.77 | 2390.21 | 430.08 |
| IL-12 (p40), free | 29.45 | 8.77 | 29.77 |
| MIP-1α | 136.92 | 834.62 | 609.56 |
| MIP-1β | 30.17 | 41.55 | 137.72 |
| VEGF | 54.31 | 19.95 | 36.73 |

FIGURE 2D

| PERCENT FLUORESCENCE CHANGE IN MEAN FLUORESCENCE | | | |
|---|---|---|---|
| Biomarker | LC vs. NO | AST vs. NO | AST vs. LC |
| Adiponectin | 8.308023 | 29.756609 | 16.5298599 |
| Resistin | 30.52113 | 131.39591 | 43.5940182 |
| PAI-1 | 72.02467 | 115.509824 | 20.1778046 |
| SE-selectin | -41.9987 | -38.524081 | 5.65196398 |
| sVCAM-1 | -2.14221 | 82.8602657 | 46.4849324 |
| sICAM-1 | -13.0445 | -2.1233592 | 11.1580584 |
| MPO | 318.1283 | 458.159543 | 25.0880246 |
| CRP | 42.12063 | 20.02461 | -18.409577 |
| SAA | 264.0607 | 96.0500618 | -85.697828 |
| SAP | -46.2484 | 18.3969983 | 54.6005061 |
| Leptin | -69.579 | 9.97796417 | 72.3390188 |
| GLP-1 | 133.9041 | 131.013935 | -1.2510585 |
| Amylin (Total) | 149.6069 | 188.001524 | 13.3314104 |
| C-Peptide | -43.77 | 15.6079318 | 51.3614645 |
| Insulin | -28.3602 | 52.8249719 | 53.1230023 |
| Sfas | -14.1487 | 65.0120998 | 47.972753 |
| sFSI | -32.5859 | 154.781105 | 73.5403963 |
| MIF | 103.6145 | 12.821492 | -80.474883 |
| IL-1β | 8.95437 | 76.9673003 | 38.4324848 |
| IL-2 | -26.8184 | -2.8675535 | 24.6579321 |
| IL-1ra | 19.49224 | 21.1124424 | 1.33776455 |
| IL-4 | -18.8655 | 92.8892423 | 57.9372345 |
| IL-5 | -18.5965 | 146.294659 | 66.9487515 |
| IL-6 | 55.02707 | 375.999006 | 67.4312203 |
| IL-7 | 90.62035 | 97.1867053 | 3.33001776 |
| TGF-α | 0.411397 | 34.7028941 | 25.4571344 |
| Fractalkine | 4.789211 | 27.1132799 | 17.5623423 |
| IL-8 | -64.8117 | 300.737772 | 91.2191083 |
| IL-10 | 79.03757 | 25.9054886 | -42.199971 |
| IL-15 | 0.349499 | 24.7932651 | 19.5874082 |
| IL-17 | 38.98752 | 58.0586958 | 12.0658817 |
| IL-1α | -42.0762 | 252.257187 | 83.5563807 |
| IFN-γ | 10.33321 | 22.3173905 | 9.79761046 |
| G-CSF | 5.06491 | 35.9358549 | 22.7099358 |
| GM-CSF | 3.606656 | 45.1976606 | 28.6444042 |
| TNF-α | 128.8153 | 121.889912 | -3.1211056 |
| MCP-1 | 200.7569 | 1017.85782 | 73.0952475 |
| IL-12 (p40), free | -10.1185 | 21.8436008 | 26.2320627 |
| MIP-1α | 60.73545 | 244.225273 | 53.3051572 |
| MIP-1β | 88.94775 | 48.82232 | -26.96197 |
| VEGF | -1.96318 | 30.7326781 | 25.0097033 |

FIGURE 2E

| SIGNIFICANCE OF POPULATION DIFFERENCES EXPRESSED AS PROBABILITY OF STUDENT'S T VALUE | | | |
|---|---|---|---|
| Biomarker | T LC vs. NO | T AST vs. NO | T AST vs. LC |
| Adiponectin | 0.306 | 0.001 | 0.039 |
| Resistin | 0.007 | 0.000 | 0.000 |
| PAI-1 | 0.000 | 0.000 | 0.000 |
| SE-selectin | 0.000 | 0.000 | 0.723 |
| sVCAM-1 | 0.526 | 0.000 | 0.000 |
| sICAM-1 | 0.014 | 0.700 | 0.043 |
| MPO | 0.000 | 0.000 | 0.001 |
| CRP | 0.000 | 0.022 | 0.016 |
| SAA | 0.000 | 0.000 | 0.000 |
| SAP | 0.000 | 0.000 | 0.000 |
| Leptin | 0.000 | 0.486 | 0.000 |
| GLP-1 | 0.157 | 0.112 | 0.985 |
| Amylin (Total) | 0.032 | 0.019 | 0.755 |
| C-Peptide | 0.000 | 0.006 | 0.000 |
| Insulin | 0.151 | 0.145 | 0.061 |
| Sfas | 0.647 | 0.073 | 0.000 |
| sFSI | 0.000 | 0.000 | 0.000 |
| MIF | 0.001 | 0.490 | 0.011 |
| IL-1β | 0.037 | 0.111 | 0.204 |
| IL-2 | 0.444 | 0.944 | 0.000 |
| IL-1ra | 0.035 | 0.046 | 0.632 |
| IL-4 | 0.001 | 0.000 | 0.000 |
| IL-5 | 0.046 | 0.000 | 0.000 |
| IL-6 | 0.193 | 0.008 | 0.053 |
| IL-7 | 0.130 | 0.000 | 0.933 |
| TGF-α | 0.888 | 0.000 | 0.000 |
| Fractalkine | 0.079 | 0.000 | 0.000 |
| IL-8 | 0.002 | 0.000 | 0.000 |
| IL-10 | 0.075 | 0.000 | 0.357 |
| IL-15 | 0.841 | 0.000 | 0.000 |
| IL-17 | 0.000 | 0.000 | 0.121 |
| IL-1α | 0.005 | 0.001 | 0.001 |
| IFN-γ | 0.002 | 0.000 | 0.002 |
| G-CSF | 0.341 | 0.000 | 0.000 |
| GM-CSF | 0.411 | 0.000 | 0.000 |
| TNF-α | 0.224 | 0.064 | 0.965 |
| MCP-1 | 0.000 | 0.005 | 0.042 |
| IL-12 (p40), free | 0.006 | 0.000 | 0.000 |
| MIP-1α | 0.034 | 0.117 | 0.302 |
| MIP-1β | 0.058 | 0.002 | 0.524 |
| VEGF | 0.679 | 0.000 | 0.000 |

SEQUENCE LISTING

```
<160> NUMBER OF SEQ ID NOS: 11

<210> SEQ ID NO 1
<211> LENGTH: 319
<212> TYPE: PRT
<213> ORGANISM: Homo sapien

<400> SEQUENCE: 1

Met Val Leu Ser Glu Leu Ala Ala Arg Leu Asn Cys Ala Glu Tyr
                 5                  10                  15

Lys Asn Trp Val Lys Ala Gly His Cys Leu Leu Leu Leu Arg Ser
                20                  25                  30

Cys Leu Gln Gly Phe Val Gly Arg Glu Val Leu Ser Phe His Arg
                35                  40                  45

Gly Leu Leu Ala Ala Ala Pro Gly Leu Gly Pro Arg Ala Val Cys
                50                  55                  60

Arg Gly Gly Ser Arg Cys Ser Pro Arg Ala Arg Gln Phe Gln Pro
                65                  70                  75

Gln Cys Gln Val Cys Ala Glu Trp Lys Arg Glu Ile Leu Arg His
                80                  85                  90

His Val Asn Arg Asn Gly Asp Val His Trp Gly Asn Cys Arg Pro
                95                 100                 105

Gly Arg Trp Pro Val Asp Ala Trp Glu Val Ala Lys Ala Phe Met
```

```
                        110                 115                 120
Pro Arg Gly Leu Ala Asp Lys Gln Gly Pro Glu Glu Cys Asp Ala
            125                 130                 135
Val Ala Leu Leu Ser Leu Ile Asn Ser Cys Asp His Phe Val Val
            140                 145                 150
Asp Arg Lys Lys Val Thr Glu Val Ile Lys Cys Arg Asn Glu Ile
            155                 160                 165
Met His Ser Ser Glu Met Lys Val Ser Ser Thr Trp Leu Arg Asp
            170                 175                 180
Phe Gln Met Lys Ile Gln Asn Phe Leu Asn Glu Phe Lys Asn Ile
            185                 190                 195
Pro Glu Ile Val Ala Val Tyr Ser Arg Ile Glu Gln Leu Leu Thr
            200                 205                 210
Ser Asp Trp Ala Val His Ile Pro Glu Glu Asp Gln Arg Asp Gly
            215                 220                 225
Cys Glu Cys Glu Met Gly Thr Tyr Leu Ser Gly Ser Gln Val Asn
            230                 235                 240
Glu Ile Glu Met Gln Leu Leu Lys Glu Lys Leu Gln Glu Ile Tyr
            245                 250                 255
Leu Gln Ala Glu Glu Gln Glu Val Leu Pro Glu Glu Leu Ser Asn
            260                 265                 270
Arg Leu Glu Val Val Lys Glu Phe Leu Arg Asn Asn Glu Asp Leu
            275                 280                 285
Arg Asn Gly Leu Thr Glu Asp Met Gln Lys Leu Asp Ser Leu Cys
            290                 295                 300
Leu His Gln Lys Leu Asp Ser Gln Glu Pro Gly Arg Gln Thr Pro
            305                 310                 315
Asp Arg Lys Ala

<210> SEQ ID NO 2
<211> LENGTH: 57
<212> TYPE: PRT
<213> ORGANISM: Homo sapiens

<400> SEQUENCE: 2

Met Ser Cys Leu Met Val Glu Arg Cys Gly Glu Ile Leu Phe Glu
                  5                  10                  15
Asn Pro Asp Gln Asn Ala Lys Cys Val Cys Met Leu Gly Asp Ile
                 20                  25                  30
Arg Leu Arg Gly Gln Thr Gly Val Arg Ala Glu Arg Gly Ser
                 35                  40                  45
Tyr Pro Phe Ile Asp Phe Arg Leu Leu Asn Ser Glu
                 50                  55

<210> SEQ ID NO 3
<211> LENGTH: 62
<212> TYPE: PRT
<213> ORGANISM: Homo sapiens

<400> SEQUENCE: 3

Met Ile Arg Ser Lys Phe Arg Val Pro Arg Ile Leu His Val Leu
                  5                  10                  15
Ser Ala His Ser Gln Ala Ser Asp Lys Asn Phe Thr Ala Glu Asn
                 20                  25                  30
Ser Glu Val Val Val Ser Ser Arg Thr Asp Val Ser Pro Met Lys
                 35                  40                  45
```

-continued

```
Ser Asp Leu Leu Leu Pro Pro Ser Lys Pro Gly Cys Asn Asn Val
                50                  55                  60

Leu Asn

<210> SEQ ID NO 4
<211> LENGTH: 146
<212> TYPE: PRT
<213> ORGANISM: Homo sapiens

<400> SEQUENCE: 4

Met Val Gln Gly Met Cys Ser Pro Ser Phe Gly Thr Ser Arg
                 5                  10                  15

Ala Cys Thr Val Gly Thr Gln Val Asp Ser Arg Ser Leu Pro Trp
                20                  25                  30

Ala Leu Gly Ala Ser Ala Gln Arg Gly Asn Ile Pro Thr Ala Thr
                35                  40                  45

Cys Ala Arg Thr Ala Gly Thr Leu Arg Arg Gly Leu Gln Pro Gly
                50                  55                  60

Trp Gly Trp Glu Asp Phe Leu Asp Glu Gly Gln Pro Gly Phe Ser
                65                  70                  75

Ser Arg Met Ser Trp Ser Arg Pro Pro Ala Gln Glu Gln Gly Ala
                80                  85                  90

Gly Arg Gly Pro Ser Trp Val Arg Gly Leu Gly Gln Pro Thr Ala
                95                  100                 105

Ala Phe Glu Gln Gly Pro Arg Ser Ser Val Ser Pro Gln Trp Glu
                110                 115                 120

Gly Gly Gly Gln Gly Pro Gly Glu Leu Gly Arg Lys His Leu Leu
                125                 130                 135

Gly Pro Ser Gln His His Pro Thr Asp Arg His
                140                 145

<210> SEQ ID NO 5
<211> LENGTH: 1039
<212> TYPE: PRT
<213> ORGANISM: Homo sapiens

<400> SEQUENCE: 5

Met Ala Val Gln Leu Val Pro Asp Ser Ala Leu Gly Leu Leu Met
                 5                  10                  15

Met Thr Glu Gly Arg Arg Cys Gln Val His Leu Leu Asp Asp Arg
                20                  25                  30

Lys Leu Glu Leu Leu Val Gln Pro Lys Leu Leu Ala Lys Glu Leu
                35                  40                  45

Leu Asp Leu Val Ala Ser His Phe Asn Leu Lys Glu Lys Glu Tyr
                50                  55                  60

Phe Gly Ile Ala Phe Thr Asp Glu Thr Gly His Leu Asn Trp Leu
                65                  70                  75

Gln Leu Asp Arg Arg Val Leu Glu His Asp Phe Pro Lys Lys Ser
                80                  85                  90

Gly Pro Val Val Leu Tyr Phe Cys Val Arg Phe Tyr Ile Glu Ser
                95                  100                 105

Ile Ser Tyr Leu Lys Asp Asn Ala Thr Ile Glu Leu Phe Phe Leu
                110                 115                 120

Asn Ala Lys Ser Cys Ile Tyr Lys Glu Leu Ile Asp Val Asp Ser
                125                 130                 135

Glu Val Val Phe Glu Leu Ala Ser Tyr Ile Leu Gln Glu Ala Lys
                140                 145                 150
```

```
Gly Asp Phe Ser Ser Asn Glu Val Val Arg Ser Asp Leu Lys Lys
                155                 160                 165

Leu Pro Ala Leu Pro Thr Gln Ala Leu Lys Glu His Pro Ser Leu
            170                 175                 180

Ala Tyr Cys Glu Asp Arg Val Ile Glu His Tyr Lys Lys Leu Asn
            185                 190                 195

Gly Gln Thr Arg Gly Gln Ala Ile Val Asn Tyr Met Ser Ile Val
            200                 205                 210

Glu Ser Leu Pro Thr Tyr Gly Val His Tyr Tyr Ala Val Lys Asp
            215                 220                 225

Lys Gln Gly Ile Pro Trp Trp Leu Gly Leu Ser Tyr Lys Gly Ile
            230                 235                 240

Phe Gln Tyr Asp Tyr His Asp Lys Val Lys Pro Arg Lys Ile Phe
            245                 250                 255

Gln Trp Arg Gln Leu Glu Asn Leu Tyr Phe Arg Glu Lys Lys Phe
            260                 265                 270

Ser Val Glu Val His Asp Pro Arg Arg Ala Ser Val Thr Arg Arg
            275                 280                 285

Thr Phe Gly His Ser Gly Ile Ala Val His Thr Trp Tyr Ala Cys
            290                 295                 300

Pro Ala Leu Ile Lys Ser Ile Trp Ala Met Ala Ile Ser Gln His
            305                 310                 315

Gln Phe Tyr Leu Asp Arg Lys Gln Ser Lys Ser Lys Ile His Ala
            320                 325                 330

Ala Arg Ser Leu Ser Glu Ile Ala Ile Asp Leu Thr Glu Thr Gly
            335                 340                 345

Thr Leu Lys Thr Ser Lys Leu Ala Asn Met Gly Ser Lys Gly Lys
            350                 355                 360

Ile Ile Ser Gly Ser Ser Gly Ser Leu Leu Ser Ser Gly Ser Gln
            365                 370                 375

Glu Ser Asp Ser Ser Gln Ser Ala Lys Lys Asp Met Leu Ala Ala
            380                 385                 390

Leu Lys Ser Arg Gln Glu Ala Leu Glu Glu Thr Leu Arg Gln Arg
            395                 400                 405

Leu Glu Glu Leu Lys Lys Leu Cys Leu Arg Glu Ala Glu Leu Thr
            410                 415                 420

Gly Lys Leu Pro Val Glu Tyr Pro Leu Asp Pro Gly Glu Glu Pro
            425                 430                 435

Pro Ile Val Arg Arg Arg Ile Gly Thr Ala Phe Lys Leu Asp Glu
            440                 445                 450

Gln Lys Ile Leu Pro Lys Gly Glu Glu Ala Glu Leu Glu Arg Leu
            455                 460                 465

Glu Arg Glu Phe Ala Ile Gln Ser Gln Ile Thr Glu Ala Ala Arg
            470                 475                 480

Arg Leu Ala Ser Asp Pro Asn Val Ser Lys Lys Leu Lys Lys Gln
            485                 490                 495

Arg Lys Thr Ser Tyr Leu Asn Ala Leu Lys Lys Leu Gln Glu Ile
            500                 505                 510

Glu Asn Ala Ile Asn Glu Asn Arg Ile Lys Ser Gly Lys Lys Pro
            515                 520                 525

Thr Gln Arg Ala Ser Leu Ile Ile Asp Asp Gly Asn Ile Ala Ser
            530                 535                 540

Glu Asp Ser Ser Leu Ser Asp Ala Leu Val Leu Glu Asp Glu Asp
```

```
                    545                 550                 555
Ser Gln Val Thr Ser Thr Ile Ser Pro Leu His Ser Pro His Lys
                560                 565                 570
Gly Leu Pro Pro Arg Pro Ser His Asn Arg Pro Pro Pro
            575                 580                 585
Gln Ser Leu Glu Gly Leu Arg Gln Met His Tyr His Arg Asn Asp
        590                 595                 600
Tyr Asp Lys Ser Pro Ile Lys Pro Lys Met Trp Ser Glu Ser Ser
    605                 610                 615
Leu Asp Glu Pro Tyr Glu Lys Val Lys Lys Arg Ser Ser His Ser
620                 625                 630
His Ser Ser Ser His Lys Arg Phe Pro Ser Thr Gly Ser Cys Ala
            635                 640                 645
Glu Ala Gly Gly Gly Ser Asn Ser Leu Gln Asn Ser Pro Ile Arg
        650                 655                 660
Gly Leu Pro His Trp Asn Ser Gln Ser Ser Met Pro Ser Thr Pro
    665                 670                 675
Asp Leu Arg Val Arg Ser Pro His Tyr Val His Ser Thr Arg Ser
680                 685                 690
Val Asp Ile Ser Pro Thr Arg Leu His Ser Leu Ala Leu His Phe
            695                 700                 705
Arg His Arg Ser Ser Ser Leu Glu Ser Gln Gly Lys Leu Leu Gly
        710                 715                 720
Ser Glu Asn Asp Thr Gly Ser Pro Asp Phe Tyr Thr Pro Arg Thr
    725                 730                 735
Arg Ser Ser Asn Gly Ser Asp Pro Met Asp Asp Cys Ser Ser Cys
740                 745                 750
Thr Ser His Ser Ser Ser Glu His Tyr Tyr Pro Ala Gln Met Asn
            755                 760                 765
Ala Asn Tyr Ser Thr Leu Ala Glu Asp Ser Pro Ser Lys Ala Arg
        770                 775                 780
Gln Arg Gln Arg Gln Arg Gln Arg Ala Ala Gly Ala Leu Gly Ser
    785                 790                 795
Ala Ser Ser Gly Ser Met Pro Asn Leu Ala Ala Arg Gly Gly Ala
800                 805                 810
Gly Gly Ala Gly Gly Ala Gly Gly Val Tyr Leu His Ser Gln
            815                 820                 825
Ser Gln Pro Ser Ser Gln Tyr Arg Ile Lys Glu Tyr Pro Leu Tyr
        830                 835                 840
Ile Glu Gly Gly Ala Thr Pro Val Val Arg Ser Leu Glu Ser
    845                 850                 855
Asp Gln Glu Gly His Tyr Ser Val Lys Ala Gln Phe Lys Thr Ser
860                 865                 870
Asn Ser Tyr Thr Ala Gly Gly Leu Phe Lys Glu Ser Trp Arg Gly
            875                 880                 885
Gly Gly Gly Asp Glu Gly Asp Thr Gly Arg Leu Thr Pro Ser Arg
        890                 895                 900
Ser Gln Ile Leu Arg Thr Pro Ser Leu Gly Arg Glu Gly Ala His
    905                 910                 915
Asp Lys Gly Ala Gly Arg Ala Ala Val Ser Asp Glu Leu Arg Gln
920                 925                 930
Trp Tyr Gln Arg Ser Thr Ala Ser His Lys Glu His Ser Arg Leu
            935                 940                 945
```

```
Ser His Thr Ser Ser Thr Ser Asp Ser Gly Ser Gln Tyr Ser
            950                 955                 960

Thr Ser Ser Gln Ser Thr Phe Val Ala His Ser Arg Val Thr Arg
                965                 970                 975

Met Pro Gln Met Cys Lys Ala Thr Ser Ala Ala Leu Pro Gln Ser
                980                 985                 990

Gln Arg Ser Ser Thr Pro Ser Ser Glu Ile Gly Ala Thr Pro Pro
                995                 1000                1005

Ser Ser Pro His His Ile Leu Thr Trp Gln Thr Gly Glu Ala Thr
                1010                1015                1020

Glu Asn Ser Pro Ile Leu Asp Gly Ser Glu Ser Pro Pro His Gln
                1025                1030                1035

Ser Thr Asp Glu

<210> SEQ ID NO 6
<211> LENGTH: 244
<212> TYPE: PRT
<213> ORGANISM: Homo sapiens

<400> SEQUENCE: 6

Met Ala Ala Ala Ala Ser Pro Ala Ile Leu Pro Arg Leu Ala Ile
                 5                  10                  15

Leu Pro Tyr Leu Leu Phe Asp Trp Ser Gly Thr Gly Arg Ala Asp
                20                  25                  30

Ala His Ser Leu Trp Tyr Asn Phe Thr Ile Ile His Leu Pro Arg
                35                  40                  45

His Gly Gln Gln Trp Cys Glu Val Gln Ser Gln Val Asp Gln Lys
                50                  55                  60

Asn Phe Leu Ser Tyr Asp Cys Gly Ser Asp Lys Val Leu Ser Met
                65                  70                  75

Gly His Leu Glu Glu Gln Leu Tyr Ala Thr Asp Ala Trp Gly Lys
                80                  85                  90

Gln Leu Glu Met Leu Arg Glu Val Gly Gln Arg Leu Arg Leu Glu
                95                  100                 105

Leu Ala Asp Thr Glu Leu Glu Asp Phe Thr Pro Ser Gly Pro Leu
                110                 115                 120

Thr Leu Gln Val Arg Met Ser Cys Glu Cys Glu Ala Asp Gly Tyr
                125                 130                 135

Ile Arg Gly Ser Trp Gln Phe Ser Phe Asp Gly Arg Lys Phe Leu
                140                 145                 150

Leu Phe Asp Ser Asn Asn Arg Lys Trp Thr Val Val His Ala Gly
                155                 160                 165

Ala Arg Arg Met Lys Glu Lys Trp Glu Lys Asp Ser Gly Leu Thr
                170                 175                 180

Thr Phe Phe Lys Met Val Ser Met Arg Asp Cys Lys Ser Trp Leu
                185                 190                 195

Arg Asp Phe Leu Met His Arg Lys Lys Arg Leu Glu Pro Thr Ala
                200                 205                 210

Pro Pro Thr Met Ala Pro Gly Leu Ala Gln Pro Lys Ala Ile Ala
                215                 220                 225

Thr Thr Leu Ser Pro Trp Ser Phe Leu Ile Ile Leu Cys Phe Ile
                230                 235                 240

Leu Pro Gly Ile

<210> SEQ ID NO 7
```

```
<211> LENGTH: 536
<212> TYPE: PRT
<213> ORGANISM: Homo sapiens

<400> SEQUENCE: 7

Met Glu Ile Arg Gln His Glu Trp Leu Ser Ala Ser Pro His Glu
 1               5                  10                  15

Gly Phe Glu Gln Met Arg Leu Lys Ser Arg Pro Lys Glu Pro Ser
                20                  25                  30

Pro Ser Leu Thr Arg Val Gly Ala Asn Phe Tyr Ser Ser Val Lys
                35                  40                  45

Gln Gln Asp Tyr Ser Ala Ser Val Trp Leu Arg Arg Lys Asp Lys
                50                  55                  60

Leu Glu His Ser Gln Gln Lys Cys Ile Val Ile Phe Ala Leu Val
                65                  70                  75

Cys Cys Phe Ala Ile Leu Val Ala Leu Ile Phe Ser Ala Val Asp
                80                  85                  90

Ile Met Gly Glu Asp Glu Asp Gly Leu Ser Glu Lys Asn Cys Gln
                95                 100                 105

Asn Lys Cys Arg Ile Ala Leu Val Glu Asn Ile Pro Glu Gly Leu
               110                 115                 120

Asn Tyr Ser Glu Asn Ala Pro Phe His Leu Ser Leu Phe Gln Gly
               125                 130                 135

Trp Met Asn Leu Leu Asn Met Ala Lys Lys Ser Val Asp Ile Val
               140                 145                 150

Ser Ser His Trp Asp Leu Asn His Thr His Pro Ser Ala Cys Gln
               155                 160                 165

Gly Gln Arg Leu Phe Glu Lys Leu Leu Gln Leu Thr Ser Gln Asn
               170                 175                 180

Ile Glu Ile Lys Leu Val Ser Asp Val Thr Ala Asp Ser Lys Val
               185                 190                 195

Leu Glu Ala Leu Lys Leu Lys Gly Ala Glu Val Thr Tyr Met Asn
               200                 205                 210

Met Thr Ala Tyr Asn Lys Gly Arg Leu Gln Ser Ser Phe Trp Ile
               215                 220                 225

Val Asp Lys Gln His Val Tyr Ile Gly Ser Ala Gly Leu Asp Trp
               230                 235                 240

Gln Ser Leu Gly Gln Met Lys Glu Leu Gly Val Ile Phe Tyr Asn
               245                 250                 255

Cys Ser Cys Leu Val Leu Asp Leu Gln Arg Ile Phe Ala Leu Tyr
               260                 265                 270

Ser Ser Leu Lys Phe Lys Ser Arg Val Pro Gln Thr Trp Ser Lys
               275                 280                 285

Arg Leu Tyr Gly Val Tyr Asp Asn Glu Lys Lys Leu Gln Leu Gln
               290                 295                 300

Leu Asn Glu Thr Lys Ser Gln Ala Phe Val Ser Asn Ser Pro Lys
               305                 310                 315

Leu Phe Cys Pro Lys Asn Arg Ser Phe Asp Ile Asp Ala Ile Tyr
               320                 325                 330

Ser Val Ile Asp Asp Ala Lys Gln Tyr Val Tyr Ile Ala Val Met
               335                 340                 345

Asp Tyr Leu Pro Ile Ser Ser Thr Ser Thr Lys Arg Thr Tyr Trp
               350                 355                 360

Pro Asp Leu Asp Ala Lys Ile Arg Glu Ala Leu Val Leu Arg Ser
               365                 370                 375
```

```
Val Arg Val Arg Leu Leu Leu Ser Phe Trp Lys Glu Thr Asp Pro
            380                 385                 390

Leu Thr Phe Asn Phe Ile Ser Ser Leu Lys Ala Ile Cys Thr Glu
            395                 400                 405

Ile Ala Asn Cys Ser Leu Lys Val Lys Phe Phe Asp Leu Glu Arg
            410                 415                 420

Glu Asn Ala Cys Ala Thr Lys Glu Gln Lys Asn His Thr Phe Pro
            425                 430                 435

Arg Leu Asn Arg Asn Lys Tyr Met Val Thr Asp Gly Ala Ala Tyr
            440                 445                 450

Ile Gly Asn Phe Asp Trp Val Gly Asn Asp Phe Thr Gln Asn Ala
            455                 460                 465

Gly Thr Gly Leu Val Ile Asn Gln Ala Asp Val Arg Asn Asn Arg
            470                 475                 480

Ser Ile Ile Lys Gln Leu Lys Asp Val Phe Glu Arg Asp Trp Tyr
            485                 490                 495

Ser Pro Tyr Ala Lys Thr Leu Gln Pro Thr Lys Gln Pro Asn Cys
            500                 505                 510

Ser Ser Leu Phe Lys Leu Lys Pro Leu Ser Asn Lys Thr Ala Thr
            515                 520                 525

Asp Asp Thr Gly Gly Lys Asp Pro Arg Asn Val
            530                 535

<210> SEQ ID NO 8
<211> LENGTH: 344
<212> TYPE: PRT
<213> ORGANISM: Homo sapiens

<400> SEQUENCE: 8

Gln Asn Leu Pro Ser Ser Pro Ala Pro Ser Thr Ile Phe Ser Gly
              5                  10                  15

Gly Phe Arg His Gly Ser Leu Ile Ser Ile Asp Ser Thr Cys Thr
             20                  25                  30

Glu Met Gly Asn Phe Asp Asn Ala Asn Val Thr Gly Glu Ile Glu
             35                  40                  45

Phe Ala Ile His Tyr Cys Phe Lys Thr His Ser Leu Glu Ile Cys
             50                  55                  60

Ile Lys Ala Cys Lys Asn Leu Ala Tyr Gly Glu Glu Lys Lys Lys
             65                  70                  75

Lys Cys Asn Pro Tyr Val Lys Thr Tyr Leu Leu Pro Asp Arg Ser
             80                  85                  90

Ser Gln Gly Lys Arg Lys Thr Gly Val Gln Arg Asn Thr Val Asp
             95                 100                 105

Pro Thr Phe Gln Glu Thr Leu Lys Tyr Gln Val Ala Pro Ala Gln
            110                 115                 120

Leu Val Thr Arg Gln Leu Gln Val Ser Val Trp His Leu Gly Thr
            125                 130                 135

Leu Ala Arg Arg Val Phe Leu Gly Glu Val Ile Ile Ser Leu Ala
            140                 145                 150

Thr Trp Asp Phe Glu Asp Ser Thr Thr Gln Ser Phe Arg Trp His
            155                 160                 165

Pro Leu Arg Ala Lys Ala Glu Lys Tyr Glu Asp Ser Val Pro Gln
            170                 175                 180

Ser Asn Gly Glu Leu Thr Val Arg Ala Lys Leu Val Leu Pro Ser
            185                 190                 195
```

```
Arg Pro Arg Lys Leu Gln Glu Ala Gln Glu Gly Thr Asp Gln Pro
                200                 205                 210

Ser Leu His Gly Gln Leu Cys Leu Val Val Leu Gly Ala Lys Asn
                215                 220                 225

Leu Pro Val Arg Pro Asp Gly Thr Leu Asn Ser Phe Val Lys Gly
                230                 235                 240

Cys Leu Thr Leu Pro Asp Gln Gln Lys Leu Arg Leu Lys Ser Pro
                245                 250                 255

Val Leu Arg Lys Gln Ala Cys Pro Gln Trp Lys His Ser Phe Val
                260                 265                 270

Phe Ser Gly Val Thr Pro Ala Gln Leu Arg Gln Ser Ser Leu Glu
                275                 280                 285

Leu Thr Val Trp Asp Gln Ala Leu Phe Gly Met Asn Asp Arg Leu
                290                 295                 300

Leu Gly Gly Thr Arg Leu Gly Ser Lys Gly Asp Thr Ala Val Gly
                305                 310                 315

Gly Asp Ala Cys Ser Leu Ser Lys Leu Gln Trp Gln Lys Val Leu
                320                 325                 330

Ser Ser Pro Asn Leu Trp Thr Asp Met Thr Leu Val Leu His

<210> SEQ ID NO 9
<211> LENGTH: 263
<212> TYPE: PRT
<213> ORGANISM: Homo sapiens

<400> SEQUENCE: 9

Met Phe Arg Asn Gln Tyr Asp Asn Asp Val Thr Val Trp Ser Pro
                5                   10                  15

Gln Gly Arg Ile His Gln Ile Glu Tyr Ala Met Glu Ala Val Lys
                20                  25                  30

Gln Gly Ser Ala Thr Val Gly Leu Lys Ser Lys Thr His Ala Val
                35                  40                  45

Leu Val Ala Leu Lys Arg Ala Gln Ser Glu Leu Ala Ala His Gln
                50                  55                  60

Lys Lys Ile Leu His Val Asp Asn His Ile Gly Ile Ser Ile Ala
                65                  70                  75

Gly Leu Thr Ala Asp Ala Arg Leu Leu Cys Asn Phe Met Arg Gln
                80                  85                  90

Glu Cys Leu Asp Ser Arg Phe Val Phe Asp Arg Pro Leu Pro Val
                95                  100                 105

Ser Arg Leu Val Ser Leu Ile Gly Ser Lys Thr Gln Ile Pro Thr
                110                 115                 120

Gln Arg Tyr Gly Arg Arg Pro Tyr Gly Val Gly Leu Leu Ile Ala
                125                 130                 135

Gly Tyr Asp Asp Met Gly Pro His Ile Phe Gln Thr Cys Pro Ser
                140                 145                 150

Ala Asn Tyr Phe Asp Cys Arg Ala Met Ser Ile Gly Ala Arg Ser
                155                 160                 165

Gln Ser Ala Arg Thr Tyr Leu Glu Arg His Met Ser Glu Phe Met
                170                 175                 180

Glu Cys Asn Leu Asn Glu Leu Val Lys His Gly Leu Arg Ala Leu
                185                 190                 195

Arg Glu Thr Leu Pro Ala Glu Gln Asp Leu Thr Thr Lys Asn Val
                200                 205                 210
```

```
Ser Ile Gly Ile Val Gly Lys Asp Leu Glu Phe Thr Ile Tyr Asp
            215                 220                 225

Asp Asp Asp Val Ser Pro Phe Leu Glu Gly Leu Glu Glu Arg Pro
            230                 235                 240

Gln Arg Lys Ala Gln Pro Ala Gln Pro Ala Asp Glu Pro Ala Glu
            245                 250                 255

Lys Ala Asp Glu Pro Met Glu His
            260
```

<210> SEQ ID NO 10
<211> LENGTH: 287
<212> TYPE: PRT
<213> ORGANISM: Homo sapiens

<400> SEQUENCE: 10

```
Met Lys Asp Arg Leu Ala Glu Leu Leu Asp Leu Ser Lys Gln Tyr
                  5                  10                  15

Asp Gln Gln Phe Pro Asp Gly Asp Glu Phe Asp Ser Pro His
                 20                  25                  30

Glu Asp Ile Val Phe Glu Thr Asp His Ile Leu Glu Ser Leu Tyr
                 35                  40                  45

Arg Asp Ile Arg Asp Ile Gln Asp Glu Asn Gln Leu Leu Val Ala
                 50                  55                  60

Asp Val Lys Arg Leu Gly Lys Gln Asn Ala Arg Phe Leu Thr Ser
                 65                  70                  75

Met Arg Arg Leu Ser Ser Ile Lys Arg Asp Thr Asn Ser Ile Ala
                 80                  85                  90

Lys Ala Ile Lys Ala Arg Gly Glu Val Ile His Cys Lys Leu Arg
                 95                 100                 105

Ala Met Lys Glu Leu Ser Glu Ala Ala Glu Ala Gln His Gly Pro
                110                 115                 120

His Ser Ala Val Ala Arg Ile Ser Arg Ala Gln Tyr Asn Ala Leu
                125                 130                 135

Thr Leu Thr Phe Gln Arg Ala Met His Asp Tyr Asn Gln Ala Glu
                140                 145                 150

Met Lys Gln Arg Asp Asn Cys Lys Ile Arg Ile Gln Arg Gln Leu
                155                 160                 165

Glu Ile Met Gly Lys Glu Val Ser Gly Asp Gln Ile Glu Asp Met
                170                 175                 180

Phe Glu Gln Gly Lys Trp Asp Val Phe Ser Glu Asn Leu Leu Ala
                185                 190                 195

Asp Val Lys Gly Ala Arg Ala Ala Leu Asn Glu Ile Glu Ser Arg
                200                 205                 210

His Arg Glu Leu Leu Arg Leu Glu Ser Arg Ile Arg Asp Val His
                215                 220                 225

Glu Leu Phe Leu Gln Met Ala Val Leu Val Glu Lys Gln Ala Asp
                230                 235                 240

Thr Leu Asn Val Ile Glu Leu Asn Val Gln Lys Thr Val Asp Tyr
                245                 250                 255

Thr Gly Gln Ala Lys Ala Gln Val Arg Lys Ala Val Gln Tyr Glu
                260                 265                 270

Glu Lys Asn Pro Cys Arg Thr Leu Cys Cys Phe Cys Cys Pro Cys
                275                 280                 285

Leu Lys
```

```
-continued

<210> SEQ ID NO 11
<211> LENGTH: 244
<212> TYPE: PRT
<213> ORGANISM: Homo sapiens

<400> SEQUENCE: 11

Met Ala Ala Ala Ala Ser Pro Ala Ile Leu Pro Arg Leu Ala Ile
                    5                  10                 15

Leu Pro Tyr Leu Leu Phe Asp Trp Ser Gly Thr Gly Arg Ala Asp
                20                  25                 30

Ala His Ser Leu Trp Tyr Asn Phe Thr Ile Ile His Leu Pro Arg
                35                  40                 45

His Gly Gln Gln Trp Cys Glu Val Gln Ser Gln Val Asp Gln Lys
                50                  55                 60

Asn Phe Leu Ser Tyr Asp Cys Gly Ser Asp Lys Val Leu Ser Met
                65                  70                 75

Gly His Leu Glu Glu Gln Leu Tyr Ala Thr Asp Ala Trp Gly Lys
                80                  85                 90

Gln Leu Glu Met Leu Arg Glu Val Gly Gln Arg Leu Arg Leu Glu
                95                 100                105

Leu Ala Asp Thr Glu Leu Glu Asp Phe Thr Pro Ser Gly Pro Leu
               110                 115                120

Thr Leu Gln Val Arg Met Ser Cys Glu Cys Glu Ala Asp Gly Tyr
               125                 130                135

Ile Arg Gly Ser Trp Gln Phe Ser Phe Asp Gly Arg Lys Phe Leu
               140                 145                150

Leu Phe Asp Ser Asn Asn Arg Lys Trp Thr Val Val His Ala Gly
               155                 160                165

Ala Arg Arg Met Lys Glu Lys Trp Glu Lys Asp Ser Gly Leu Thr
               170                 175                180

Thr Phe Phe Lys Met Val Ser Met Arg Asp Cys Lys Ser Trp Leu
               185                 190                195

Arg Asp Phe Leu Met His Arg Lys Lys Arg Leu Glu Pro Thr Ala
               200                 205                210

Pro Pro Thr Met Ala Pro Gly Leu Ala Gln Pro Lys Ala Ile Ala
               215                 220                225

Thr Thr Leu Ser Pro Trp Ser Phe Leu Ile Ile Leu Cys Phe Ile
               230                 235                240

Leu Pro Gly Ile
```

METHODS OF IDENTIFICATION, ASSESSMENT, PREVENTION AND THERAPY OF LUNG DISEASES AND KITS THEREOF

CROSS-REFERENCE TO RELATED APPLICATIONS

This application is a continuation-in-part of U.S. application Ser. Nos. 12/208,437 and 12/208,876, both filed on Sep. 11, 2008. Application Ser. No. 12/208,437 claims priority to U.S. Provisional Application No. 60/971,440, filed Sep. 11, 2007. Application Ser. No. 12/208,876 claims priority to U.S. Provisional Application No. 60/971,422, filed Sep. 11, 2007. The disclosures of each of the aforementioned applications are hereby incorporated by reference.

BACKGROUND OF THE INVENTION (a) Field of the Invention

The invention relates to the detection, identification, assessment, prevention, diagnosis, and treatment of lung disease using biomarkers and kits thereof. More specifically, the invention relates to the diagnosis of non-small cell lung cancers and reactive airway diseases by measuring and quantifying expression levels of certain specific biomarkers. More specifically, the invention relates to the identification of biomarkers present in human serum or other biological fluids, which, when found to be expressed at levels different from those found in the normal population, are indicative of pathologies associated with human lung tissues and the human respiratory system. By identifying the biomarkers associated with such pathologies, quantifying the expression levels of those biomarkers, and comparing the expression levels with those levels generally expected to present in a normal person's serum, it is possible to detect the presence of the pathologies early on in their progression through simple blood tests and characterize the progression of the pathology, as well as to differentiate among the pathologies.

(b) Description of the Related Art

Pathologies of the respiratory system, such as asthma and lung cancer, affect millions of Americans. In fact, the American Lung Association® reports that almost 20 million Americans suffer from asthma. The American Cancer Society, Inc. estimated 229,400 new cancer cases of the respiratory system and 164,840 deaths from cancers of the respiratory system in 2007 alone. While the five year survival rate of cancer cases when the cancer is detected while still localized is 46%, the five year survival rate of lung cancer patients is only 13%. Correspondingly, only 16% of lung cancers are discovered before the disease has spread. Lung cancers are generally categorized as two main types based on the pathology of the cancer cells. Each type is named for the types of cells that were transformed to become cancerous. Small cell lung cancers are derived from small cells in the human lung tissues, whereas non-small-cell lung cancers generally encompass all lung cancers that are not small-cell type. Non-small cell lung cancers are grouped together because the treatment is generally the same for all non-small-cell types. Together, non-small-cell lung cancers, or NSCLCs, make up about 75% of all lung cancers.

A major factor in the low survival rate of lung cancer patients is the fact that lung cancer is difficult to diagnose early. Current methods of diagnosing lung cancer or identifying its existence in a human are restricted to taking X-rays, Computed Tomography (CT) scans and similar tests of the lungs to physically determine the presence or absence of a tumor. Therefore, the diagnosis of lung cancer is often made only in response to symptoms which have presented for a significant period of time, and after the disease has been present in the human long enough to produce a physically detectable mass.

Similarly, current methods of detecting asthma are typically performed long after the presentation of symptoms such as recurrent wheezing, coughing, and chest tightness. Current methods of detecting asthma are typically restricted to lung function tests such as spirometry tests or challenge tests. Moreover, these tests are often ordered by the physician to be performed along with a multitude of other tests to rule out other pathologies or reactive airway diseases such as chronic obstructive pulmonary disease (COPD), bronchitis, pneumonia, and congestive heart failure.

There does not exist in the art a simple, reliable method of diagnosing pathologies of human lung tissues early in their development. Furthermore, there is not a blood test available today which is capable of indicating the presence of a particular lung tissue pathology. It is therefore desirable to develop a method to determine the existence of lung cancers early in the disease progression. It is likewise desirable to develop a method to diagnose asthma and non-small cell lung cancer and to differentiate them from each other and from other lung diseases such as infections at the earliest appearance of symptoms. It is further desirable to identify specific proteins present in human blood which, when altered in terms of relative intensities of expression, are indicative of the presence of non-small cell lung cancers and/or reactive airway disease.

SUMMARY OF THE INVENTION

The present inventors have identified a number of biomarkers which are useful for characterizing the physiologic state of a subject with regard to lung diseases, such as non-small cell lung cancer or reactive airway disease. Table 1 lists biomarkers whose expression has been found to change with one or more lung diseases. Table 2 lists biomarkers whose expression has been found to change with non-small cell lung cancer. Table 3 lists biomarkers whose expression has been found to change with reactive airway disease. Table 4 lists biomarkers whose expression has been found to differ between non-small cell lung cancer and reactive airway disease. Polypeptides comprising SEQ ID NOS: 1-11 are additional biomarkers whose expression has been found to change with one or more lung diseases. The present invention provides various diagnostic, prognostic and therapeutic methods which depend on the identification of these biomarkers.

The invention provides for a method of physiological characterization in a subject comprising determining the extent of expression of at least one biomarker Table 1 in a physiological sample of the subject, wherein the extent of expression of said at least one biomarker is indicative of a lung disease, such as of non-small cell lung cancer or reactive airway disease.

The invention provides for a method of physiological characterization in a subject comprising determining the extent of expression of at least one polypeptide selected from the group consisting of SEQ ID NOS: 1-11 in a physiological sample of the subject, wherein the extent of expression of said at least one polypeptide is indicative of a lung disease, such as non-small cell lung cancer or reactive airway disease.

The invention provides for a method of physiological characterization in a subject comprising determining the extent of expression of at least one polypeptide selected from the group consisting of SEQ ID NOS: 1-11 in a physiological sample of the subject, and determining the extent of expression of at least one biomarker from Table 1, wherein the extent of expression of said at least one polypeptide and said at least one biomarker from Table 1 is indicative of a lung disease, such as non-small cell lung cancer or reactive airway disease.

The invention provides for a method of diagnosing non-small cell lung cancer in a subject comprising determining the extent of expression at least one biomarker from Table 2 in a physiological sample of the subject, wherein the extent of expression of said at least one biomarker is indicative of the presence or development of non-small cell lung cancer.

The invention provides for a method of diagnosing reactive airway disease in a subject comprising determining the extent of expression of at least one biomarker from Table 3 in a physiological sample of the subject wherein the extent of expression of said at least one biomarker is indicative of reactive airway disease.

The invention provides for a method of diagnosing a lung disease in a subject comprising determining the extent of expression of at least one biomarker from Table 2, at least one biomarker from Table 3, and at least one biomarker from Table 4 in a physiological sample of the subject, wherein (i) said at least one biomarker from each of Table 2, Table 3, and Table 4 is not identical, (ii) the extent of expression of said at least one biomarker from Table 2 and Table 3 is indicative of the lung disease of non-small cell lung cancer and reactive airway disease, respectively; and (iii) the extent of expression of said at least one biomarker from Table 4 assists in discriminating between the indication of non-small cell lung cancer and reactive airway disease.

The invention provides a diagnostic method to assist in differentiating the likelihood that a subject is at-risk of non-small cell lung cancer or reactive airway disease comprising determining the extent of expression of at least one biomarker from Table 4 in a physiological sample of the subject who is at-risk for at least one of non-small cell lung cancer or reactive airway disease, wherein the extent of expression of said at least one biomarker from Table 4 assists in differentiating the likelihood that said subject is at-risk of non-small cell lung cancer or reactive airway disease.

The invention provides a method for predicting the likelihood that a subject will respond to therapeutic intervention comprising determining the extent of expression of at least one biomarker from Table 1 in a physiological sample of the subject, wherein the extent of expression of said at least one biomarker from Table 1 assists in predicting a subject's response to said therapeutic intervention.

The invention also provides a method of monitoring a subject comprising determining a first extent of expression of at least one biomarker from Table 1 in a physiological sample of the subject, a second extent of expression of said at least one biomarker from Table 1 in a physiological sample of the subject at a subsequent time to said first determination, and comparing said first extent of expression and said second extent of expression.

The invention also provides a kit comprising, (a) a first means for determining the extent of expression of at least one biomarker from Table 2; (b) a second means for determining the extent of expression of at least one biomarker from Table 3; and (c) a third means for determining the extent of expression of at least one biomarker from Table 4, wherein said at least one biomarker from Table 2, Table 3, and Table 4 are not identical.

The invention also provides a kit comprising, (a) detection agents for detecting at least one biomarker from Table 2; (b) detection agents for detecting at least one biomarker from Table 3; and (c) detection agents for detecting at least one biomarker from Table 4, wherein said at least one biomarker from Table 2, Table 3, and Table 4 are not identical.

The invention also provides a kit comprising a means for determining the extent of expression of at least one polypeptide selected from the group consisting of SEQ ID NOS: 1-11.

The invention also provides a kit comprising, detection agents for detecting at least one polypeptide selected from the group consisting of SEQ ID NOS: 1-11.

The invention also provides a kit comprising, (a) means for determining the extent of expression of at least one polypeptide selected from the group consisting of SEQ ID NOS: 1-11, and (b) means for determining the extent of expression of at least one biomarker from Table 1.

The invention also provides a kit comprising, (a) detection agents for detecting at least one polypeptide selected from the group consisting of SEQ ID NOS: 1-11, and (b) detection agents for detecting at least one biomarker from Table 1.

BRIEF DESCRIPTION OF THE DRAWINGS

FIG. 1A shows the average expression level of the biomarkers in the normal (NO) population from Example 1, as well as the standard deviation and relative standard deviation for expression of each biomarker.

FIG. 1B shows the average expression level of the biomarkers in the non-small cell lung cancer (LC) population from Example 1, as well as the standard deviation and relative standard deviation for expression of each biomarker.

FIG. 1C shows the average expression level of the biomarkers in the asthma (AST) population from Example 1, as well as the standard deviation and relative standard deviation for expression of each biomarker.

FIG. 1D shows the percent change in the mean of each of the biomarkers in the non-small cell lung cancer population (LC) population from the normal (NO) population, in an asthma (AST) population compared to the NO population, and between the LC and AST populations from Example 1.

FIG. 1E shows the probability associated with the Student's t statistic values for comparison of the means of the biomarkers in the populations from Example 1, where the means to be compared are non-small cell lung cancer population (LC) and normal (NO) populations, asthma (AST) and NO populations, and the LC and AST populations, respectively.

FIG. 2A shows the average expression level of the biomarkers in the normal (NO) population from Example 2, as well as the standard deviation and relative standard deviation for expression of each biomarker.

FIG. 2B shows the average expression level of the biomarkers in the non-small cell lung cancer (LC) population from Example 2, as well as the standard deviation and relative standard deviation for expression of each biomarker.

FIG. 2C shows the average expression level of the biomarkers in the asthma (AST) population from Example 2, as well as the standard deviation and relative standard deviation for expression of each biomarker.

FIG. 2D shows the percent change in the mean of each of the biomarkers in the non-small cell lung cancer population (LC) population from the normal (NO) population, in an asthma (AST) population compared to the NO population, and between the LC and AST populations from Example 2.

FIG. 2E shows the probability associated with the Student's t statistic values for comparison of the means of the biomarkers in the populations from Example 2, where the means to be compared are non-small cell lung cancer population (LC) and normal (NO) populations, asthma (AST) and NO populations, and the LC and AST populations, respectively.

DETAILED DESCRIPTION OF THE INVENTION

The invention relates to various methods of detection, identification, assessment, prevention, diagnosis, and treatment of lung disease using biomarkers. These methods involve determining the extent of expression of specific biomarkers for which an altered expression is indicative of non-small cell lung cancer and/or reactive airway disease (e.g., asthma, chronic obstructive pulmonary disease, etc.). The invention also provides for various kits comprising detection agents for detecting these biomarkers, or means for determining the extent of expression of these biomarkers.

DEFINITIONS

As used herein, a "biomarker" or "marker" is a macromolecule that is objectively measured as a characteristic indicator of the physiological status of a biological system. Biomarkers are generally polypeptides, although they may also be mRNA or modified mRNA which represents the pre-translation form of the gene product expressed as the polypeptide, or they may include post-translational modifications of the polypeptide. Table 1 below lists particular biomarkers that show a significant difference in expression level between at least one of normal (NO), non-small cell lung cancer (LC), and asthma (AST) populations. Table 2 below lists biomarkers that show significant difference in expression level between NO and LC populations. Table 3 below lists biomarkers that show significant difference in expression level between NO and AST populations. Table 4 below lists biomarkers that show significant difference in expression level between LC and AST populations.

As used herein, a "subject" means any animal, but is preferably a mammal, such as, for example, a human. In many embodiments, the subject will be a human patient having, or at-risk of having, a lung disease.

As used herein, a "physiological sample" includes samples from biological fluids and tissues. Biological fluids include whole blood, blood plasma, blood serum, sputum, urine, sweat, lymph, and alveolar lavage. Tissue samples include biopsies from solid lung tissue or other solid tissues, lymph node biopsy tissues, biopsies of metastatic foci. Method of obtaining physiological samples are well known.

As used herein, "therapeutic intervention" includes administration of one or more therapeutic agents such as a small molecule or macromolecule, radiation, surgery, or any combinations thereof.

As used herein, "detection agents" include reagents and systems that specifically detect the biomarkers described herein. Detection agents include reagents such as antibodies, nucleic acid probes, aptamers, lectins, or other reagents that have specific affinity for a particular marker or markers sufficient to discriminate between the particular marker and other markers which might be in samples of interest, and systems such as sensors, including sensors making use of bound or otherwise immobilized ligands as described above.

Identification of Biomarkers

The biomarkers of the invention were identified using two methods. First, identification of biomarkers indicative of non-small cell lung cancers and/or asthma was made by comparing the measured expression levels of fifty-nine selected biomarkers in the plasma of patients from populations known to have those respective pathologies to a population known not to have the pathologies, as confirmed by a physician. This method is detailed in Examples 1 and 2.

Second, biomarkers were identified using mass spectrometry. Selection of proteins indicative of non-small cell lung cancers and/or asthma was made by comparing the mass spectral data for tryptic peptide digests of samples obtained from patients in different physiological states. In particular, the data was the mass of peptide fragments, represented as graphical indications of the intensities of the pseudo or protonated molecular ion signals of peptides and proteins containing those fragments expressed across time in a single dimension. The expression levels of thousands of proteins were compared, resulting in the selection of eleven proteins which were expressed in substantially differing intensities between populations of individuals not having any diagnosed lung tissue pathologies, populations of individuals having asthma, as diagnosed by a physician, and populations of individuals having non-small cell lung cancers, as diagnosed by a physician. This method is detailed in Example 3.

Tables Identifying Significant Biomarkers

Table 1 lists biomarkers whose expression levels have significant difference between at least one normal (NO), non-small cell lung cancer (LC), and asthma (AST) populations. Significance was determined as shown in Examples 1 and 2 using a Student's t test.

TABLE 1

SIGNIFICANT BIOMARKERS FOR LUNG DISEASE

| No. | Biomarker |
|---|---|
| 1 | SAP |
| 2 | PAI-1 |
| 3 | sFS1 |
| 4 | SAA |
| 5 | MPO |
| 6 | EGF |
| 7 | IL-4 |
| 8 | IL-8 |
| 9 | IFN-γ |
| 10 | C-Peptide |
| 11 | IL-12 (p40), free |
| 12 | IL-1α |
| 13 | Resistin |
| 14 | CRP |
| 15 | IL-5 |
| 16 | MCP-1 |
| 17 | Fractalkine |
| 18 | IL-17 |
| 19 | MMP-7 |
| 20 | CD40 Ligand |
| 21 | IL-6 |
| 22 | MMP-13 |
| 23 | G-CSF |
| 24 | Adiponectin |
| 25 | IL-1β |
| 26 | Insulin |
| 27 | GM-CSF |
| 28 | IL-10 |
| 29 | HGF |
| 30 | MIP-1α |
| 31 | Leptin |
| 32 | MIF |
| 33 | sVCAM-1 |
| 34 | MMP-2 |
| 35 | MIP-1β |
| 36 | VEGF |
| 37 | IL-1ra |
| 38 | Sfas |
| 39 | SE-selectin |
| 40 | sICAM-1 |
| 41 | Amylin (Total) |
| 42 | IP-10 |
| 43 | MMP-12 |
| 44 | IL-15 |
| 45 | MMP-8 |
| 46 | TGF-α |
| 47 | MMP-9 |
| 48 | I-TAC |

TABLE 1-continued

SIGNIFICANT BIOMARKERS FOR LUNG DISEASE

| No. | Biomarker |
|---|---|
| 49 | MMP-3 |
| 50 | IL-7 |
| 51 | TNF-α |
| 52 | GLP-1 |
| 53 | IL-2 |

Table 2 lists biomarkers whose expression levels have significant difference between NO and LC populations. Significance was determined as shown in Examples 1 and 2 using a Student's t test.

TABLE 2

BIOMARKERS INDICATIVE OF NSCLC

| No. | Biomarker |
|---|---|
| 1 | EGF |
| 2 | CD40 Ligand |
| 3 | MMP-9 |
| 4 | SAP |
| 5 | MPO |
| 6 | C-Peptide |
| 7 | SAA |
| 8 | Leptin |
| 9 | PAI-1 |
| 10 | MCP-1 |
| 11 | CRP |
| 12 | IL-17 |
| 13 | SE-selectin |
| 14 | sFS1 |
| 15 | MIF |
| 16 | IL-4 |
| 17 | IFN-γ |
| 18 | IL-8 |
| 19 | IL-1α |
| 20 | IL-12 (p40), free |
| 21 | Resistin |
| 22 | MMP-12 |
| 23 | sICAM-1 |
| 24 | MMP-7 |
| 25 | Amylin (Total) |
| 26 | MIP-1α |
| 27 | IL-1ra |
| 28 | IL-1β |
| 29 | IL-5 |
| 30 | MIP-1β |
| 31 | IL-10 |
| 32 | Fractalkine |

Table 3 lists biomarkers whose expression levels have significant difference between NO and AST populations. Significance was determined as shown in Examples 1 and 2 using a Student's t test.

TABLE 3

BIOMARKERS INDICATIVE OF REACTIVE AIRWAY DISEASE

| No. | Biomarker |
|---|---|
| 1 | CD40 Ligand |
| 2 | sVCAM-1 |
| 3 | MPO |
| 4 | IL-7 |
| 5 | PAI-1 |
| 6 | Resistin |
| 7 | TGF-α |
| 8 | IL-17 |
| 9 | Fractalkine |
| 10 | IL-15 |

TABLE 3-continued

BIOMARKERS INDICATIVE OF REACTIVE AIRWAY DISEASE

| No. | Biomarker |
|---|---|
| 11 | G-CSF |
| 12 | IL-10 |
| 13 | IFN-γ |
| 14 | VEGF |
| 15 | IL-12 (p40), free |
| 16 | SAP |
| 17 | sFS1 |
| 18 | SE-selectin |
| 19 | GM-CSF |
| 20 | SAA |
| 21 | IL-8 |
| 22 | IL-4 |
| 23 | IL-5 |
| 24 | EGF |
| 25 | IL-1α |
| 26 | Adiponectin |
| 27 | MIP-1β |
| 28 | MCP-1 |
| 29 | C-Peptide |
| 30 | IL-6 |
| 31 | MMP-7 |
| 32 | MMP-13 |
| 33 | Amylin (Total) |
| 34 | CRP |
| 35 | HGF |
| 36 | IL-1ra |
| 37 | MMP-3 |
| 38 | TNF-α |
| 39 | MMP-12 |
| 40 | Sfas |

Table 4 lists biomarkers whose expression levels have significant difference between LC and AST populations. Significance was determined as shown in Examples 1 and 2 using a Student's t test.

TABLE 4

BIOMARKERS FOR DISCRIMINATION BETWEEN NSCLS AND REACTIVE AIRWAY DISEASE

| No. | Biomarker |
|---|---|
| 1 | EGF |
| 2 | MMP-13 |
| 3 | MMP-9 |
| 4 | sVCAM-1 |
| 5 | SAP |
| 6 | C-Peptide |
| 7 | Sfas |
| 8 | IL-15 |
| 9 | TGF-α |
| 10 | VEGF |
| 11 | IL-12 (p40), free |
| 12 | Leptin |
| 13 | IL-2 |
| 14 | Fractalkine |
| 15 | sFS1 |
| 16 | Resistin |
| 17 | PAI-1 |
| 18 | IL-8 |
| 19 | GM-CSF |
| 20 | IL-4 |
| 21 | SAA |
| 22 | IL-5 |
| 23 | G-CSF |
| 24 | IL-1α |
| 25 | MPO |
| 26 | IFN-γ |
| 27 | HGF |
| 28 | MIF |
| 29 | I-TAC |
| 30 | CRP |

TABLE 4-continued

BIOMARKERS FOR DISCRIMINATION BETWEEN
NSCLS AND REACTIVE AIRWAY DISEASE

| No. | Biomarker |
|---|---|
| 31 | Adiponectin |
| 32 | MCP-1 |
| 33 | sICAM-1 |
| 34 | IL-6 |
| 35 | IP-10 |
| 36 | MMP-2 |
| 37 | Insulin |
| 38 | MMP-8 |
| 39 | MMP-3 |

The invention provides for methods of using the biomarkers of Tables 1-4. In the descriptions of methods, using biomarkers of Table 1 may be considered exemplary. As such, the invention provides that the biomarkers of Table 2, Table 3, or Table 4 may be substituted for the biomarkers of Table 1 in any method of using the biomarkers of Table 1 described herein unless the context makes clear that a specific subset of biomarkers are intended.

Determining the Extent of Expression

Extent of expression generally relates to a quantitative measurement of an expression product which is typically a protein or polypeptide. The invention contemplates determining the extent of expression at the RNA (pre-translational) or protein level (which may include post-translational modification). In particular, the invention contemplates determining changes in biomarker concentrations reflected in an increase or decrease in the level of transcription, translation, post-transcriptional modification, or the rate of degradation of protein, where these changes are associated with a particular disease state or disease progression.

The extent of expression in a subject is proportional to the concentration of said biomarker in the sample. Typically, the extent of expression of at least one biomarker indicative of a lung disease is a level of at least one biomarker that differs by a statistically significant degree from the average expression level in normal individuals. Alternatively, at least one biomarker is statistically deviant from the normal. Statistical significance and deviation may be determined using any known method for comparing means of populations or comparing a measured value to the mean value for a population. Such methods include the Student's t tests for single and multiple markers considered together, analysis of variance (ANOVA), etc.

As shown herein, many proteins expressed by a normal subject will be expressed to a greater or lesser extent in subjects having a disease or condition, such as non-small cell lung cancer or asthma. One of skill in the art will appreciate that most diseases manifest changes in multiple, different biomarkers. As such, disease may be characterized by a pattern of expression of a plurality of markers. Indeed, changes in a pattern of expression for a plurality of biomarkers may be used in various diagnostic and prognostic methods, as well as monitoring, therapy selection, and patient assessment methods. The invention provides for such methods. These methods comprise determining a pattern of expression of a plurality of markers for a particular physiologic state, or determining changes in such a pattern which correlate to changes in physiologic state, as characterized by any technique for suitable pattern recognition.

Numerous methods of determining the extent of expression are known in the art. Means for determining expression include but are not limited to radio-immuno assay, enzyme-linked immunosorbent assay (ELISA), high pressure liquid chromatography with radiometric or spectrometric detection via absorbance of visible or ultraviolet light, mass spectrometric qualitative and quantitative analysis, western blotting, 1 or 2 dimensional gel electrophoresis with quantitative visualization by means of detection of radioactive, fluorescent or chemiluminescent probes or nuclei, antibody-based detection with absorptive or fluorescent photometry, quantitation by luminescence of any of a number of chemiluminescent reporter systems, enzymatic assays, immunoprecipitation or immuno-capture assays, solid and liquid phase immunoassays, protein arrays or chips, DNA arrays or chips, plate assays, assays that use molecules having binding affinity that permit discrimination such as aptamers and molecular imprinted polymers, and any other quantitative analytical determination of the concentration of a biomarker by any other suitable technique, instrumental actuation of any of the described detection techniques or instrumentation.

The step of determining the extent of expression may be performed by any means for determining expression known in the art, especially those means discussed herein. In preferred embodiments, the step of determining the extent of expression comprises performing an immunoassay.

Methods of Physiological Characterization

The invention provides for methods of physiological characterization in a subject. Such methods include but are not limited to predicting, diagnosing, and monitoring therapeutic intervention by determining the extent of expression of the biomarkers described herein.

In one embodiment, the invention provides for a method of physiological characterization in a subject comprising determining the extent of expression of at least one biomarker from Table 1 in a physiological sample of the subject where the extent of expression of the at least one biomarker is indicative of the lung disease of non-small cell lung cancer or reactive airway disease.

The invention provides for various methods comprising the step of determining the extent of expression of one or more biomarkers described herein. In one embodiment, the method comprises determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 biomarkers from Table 1. In another embodiment, the method comprises determining the extent of expression of any combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 biomarkers from Table 1. In another embodiment, the method comprises determining the extent of expression of any 2, 3, 4, 5, 6, 7, 8, 9, 10, 11, 12, 3, 14, 15, 16, 17, 18, or 19 biomarkers from biomarker nos. 1-20 of Table 1. In another embodiment, the method comprises determining the extent of expression of biomarker nos. 1-16 of Table 1. In another embodiment, the method comprises determining the extent of expression of biomarker nos. 1-17 of Table 1. In another embodiment, the method comprises determining the extent of expression of any combination of at least 2, 3, 4, 5, 6, 7, 8, 9, 10, 11, 12, 13, 14, or 15 biomarkers from biomarker nos. 1-16 of Table 1. In another embodiment, the method comprises determining the extent of expression of any combination of at least 2, 3, 4, 5, 6, 7, 8, 9, 10, 11, 12, 13, 14, 15, or 16 biomarkers from biomarker nos. 1-17 of Table 1. In another embodiment, the method comprises determining the extent of expression of any 2, 3, 4, 5, 6, 7, 8, or 9 biomarkers from biomarker nos. 1-10 of Table 1. In another embodiment, the method comprises determining the extent of expression of any 2, 3, 4, or 5 biomarkers from biomarker nos. 1-6 of Table 1. The invention contemplates that in any of the above embodiments the extent of expression of no more than 5, 10, 15, 20, 25, 30, 35, 40, 45, 50, or 53 biomarkers are determined.

In another embodiment, the method comprises determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 biomarkers from Table 2. In another embodiment, the method comprises determining the extent of expression of any combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 biomarkers from Table 2. In another embodiment, the method comprises determining the extent of expression of any 2, 3, 4, 5, 6, 7, 8, 9, 10, 11, 12, 3, 14, 15, 16, 17, 18, or 19 biomarkers from biomarker nos. 1-20 of Table 2. In another embodiment, the method comprises determining the extent of expression of any 2, 3, 4, 5, 6, 7, 8, or 9 biomarkers from biomarker nos. 1-10 of Table 2. In another embodiment, the method comprises determining the extent of expression of any 2, 3, 4, or 5 biomarkers from biomarker nos. 1-6 of Table 2. The invention contemplates that in any of the above embodiments the extent of expression of no more than 5, 10, 15, 20, 25, 30, or 32 biomarkers are determined.

In another embodiment, the method comprises determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 biomarkers from Table 3. In another embodiment, the method comprises determining the extent of expression of any combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 biomarkers from Table 3. In another embodiment, the method comprises determining the extent of expression of any 2, 3, 4, 5, 6, 7, 8, 9, 10, 11, 12, 3, 14, 15, 16, 17, 18, or 19 biomarkers from biomarker nos. 1-20 of Table 3. In another embodiment, the method comprises determining the extent of expression of any 2, 3, 4, 5, 6, 7, 8, or 9 biomarkers from biomarker nos. 1-10 of Table 3. In another embodiment, the method comprises determining the extent of expression of any 2, 3, 4, or 5 biomarkers from biomarker nos. 1-6 of Table 3. The invention contemplates that in any of the above embodiments the extent of expression of no more than 5, 10, 15, 20, 25, 30, 35, or 40 biomarkers are determined.

In another embodiment, the method comprises determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 biomarkers from Table 4. In another embodiment, the method comprises determining the extent of expression of any combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 biomarkers from Table 4. In another embodiment, the method comprises determining the extent of expression of any 2, 3, 4, 5, 6, 7, 8, 9, 10, 11, 12, 3, 14, 15, 16, 17, 18, or 19 biomarkers from biomarker nos. 1-20 of Table 4. In another embodiment, the method comprises determining the extent of expression of any 2, 3, 4, 5, 6, 7, 8, or 9 biomarkers from biomarker nos. 1-10 of Table 4. In another embodiment, the method comprises determining the extent of expression of any 2, 3, 4, or 5 biomarkers from biomarker nos. 1-6 of Table 4. The invention contemplates that in any of the above embodiments the extent of expression of no more than 5, 10, 15, 20, 25, 30, 35, or 39 biomarkers are determined.

In another embodiment, the method comprises determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 biomarkers from Table 2, any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 biomarkers from Table 3, and any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 biomarkers from Table 4, wherein said biomarkers are not identical. In another embodiment, the method comprises determining the extent of expression of any 2, 3, 4, 5, 6, 7, 8, 9, 10, 11, 12, 3, 14, 15, 16, 17, 18, or 19 biomarkers from biomarker nos. 1-20 of Table 2, any 2, 3, 4, 5, 6, 7, 8, 9, 10, 11, 12, 3, 14, 15, 16, 17, 18, or 19 biomarkers from biomarker nos. 1-20 of Table 3, and any 2, 3, 4, 5, 6, 7, 8, 9, 10, 11, 12, 3, 14, 15, 16, 17, 18, or 19 biomarkers from biomarker nos. 1-20 of Table 4, wherein said biomarkers are not identical. In another embodiment, the method comprises determining the extent of expression of any 2, 3, 4, 5, 6, 7, 8, or 9 biomarkers from biomarker nos. 1-10 of Table 2, any 2, 3, 4, 5, 6, 7, 8, or 9 biomarkers from biomarker nos. 1-10 of Table 3, and any 2, 3, 4, 5, 6, 7, 8, or 9 biomarkers from biomarker nos. 1-10 of Table 4, wherein said biomarkers are not identical. In another embodiment, the method comprises determining the extent of expression of any 2, 3, 4, or 5 biomarkers from biomarker nos. 1-6 of Table 2, any 2, 3, 4, or 5 biomarkers from biomarker nos. 1-6 of Table 3, and any 2, 3, 4, or 5 biomarkers from biomarker nos. 1-6 of Table 4, wherein said biomarkers are not identical. The invention contemplates that in any of the above embodiments the extent of expression of no more than 5, 10, 15, 20, 25, or biomarkers are determined.

In one embodiment, the method comprises determining the extent of expression of any one of SEQ ID NOS: 1-11. In another embodiment, the method comprises determining the extent of expression of any combination of SEQ ID NOS: 1-11.

In a preferred embodiment, the invention provides for methods of physiological characterization in a subject comprising determining the extent of expression of a plurality of biomarkers from Table 1 in a physiological sample of the subject, where a pattern of expression of the plurality of markers correlate to a physiologic state or condition, or changes in a disease state (e.g., stages in non-small cell lung cancer) or condition. In a preferred embodiment, a pattern of expression of a plurality of biomarkers from Table 1 are indicative of a lung disease such as non-small cell lung cancer or reactive airway disease. Preferably, the plurality of biomarkers are selected based on the low probability of erroneous pattern classification based on the value of Student's t as calculated in Example 1 or Example 2. In another preferred embodiment, patterns of expression of biomarkers from Table 1 correlate to an increased likelihood that a subject has or may have a particular disease or condition. In a more preferred embodiment, methods of determining the extent of expression of a plurality of biomarkers from Table 1 in a subject increase the likelihood that a subject is developing, has or may have a lung disease such as non-small cell lung cancer or reactive airway disease (e.g., asthma). Patterns of expression may be characterized by any technique known in the art for pattern recognition. The plurality of biomarkers may comprise any of the combinations of biomarkers described above with respect to Table 1.

The invention also provides for a method of physiological characterization in a subject comprising determining the extent of expression of at least one polypeptide selected from the group consisting of SEQ ID NOS: 1-11 in a physiological sample of the subject, wherein the extent of expression of said at least one polypeptide is indicative of the lung disease of non-small cell lung cancer or reactive airway disease. In a preferred embodiment, a pattern of expression of a plurality of markers of SEQ ID NOS: 1-11 are determined and used as described herein.

In one preferred mode, the invention provides for a method of physiological characterization in a subject comprising, (a) obtaining a physiological sample of the subject; (b) determining the extent of expression in said subject of at least one polypeptide selected from the group consisting of SEQ ID NOS: 1-11, and (c) determining the extent of expression in said subject of at least one biomarker from Table 1, wherein the extent of expression of both the polypeptide and the biomarker from Table 1 is indicative of a lung disease of non-small cell lung cancer or reactive airway disease. In another embodiment, a pattern of expression of a plurality of markers of SEQ ID NOS: 1-11, and a plurality of biomarkers from Table 1 are determined and used as described herein.

In one embodiment, the subject is at-risk for the lung disease of non-small cell cancer or reactive airway disease (e.g., asthma, chronic obstructive pulmonary disease, etc.). Subjects "at-risk" include those individuals who are asymptomatic but are more likely than the bulk of the population to develop the disease, because of personal or family history, behavior, exposure to disease causing agents (e.g., carcinogens), or some other reason. "At-risk" individuals are traditionally identified by aggregating the risk factors determined for the individual. The present invention provides for enhanced detection of "at-risk" individuals by determining the extent of expression of relevant biomarkers. In one embodiment, levels of particular biomarkers associated with the disease (particularly biomarkers from Table 2 or Table 3) are determined for an individual, and levels which differ from those expected for the normal population suggest that the individual is "at-risk." In another embodiment, the number of relevant biomarkers (from Table 2 or Table 3 as appropriate to the disease) which deviate statistically from normal is determined, with a greater number of deviant markers indicating greater risk.

The embodiments described above refer to the biomarkers of Table 1. It will be appreciated, however, that the biomarkers of Table 2, Table 3, or Table 4 may be substituted for the biomarkers of Table 1 in any of the described embodiments.

Lung Disease

The invention provides for various diagnostic and prognostic methods for lung disease. In particular, the invention provides methods of diagnosing non-small cell lung cancer. These methods include determining the extent of expression of at least one biomarker described herein, wherein the biomarker(s) is indicative of the presence or development of non-small lung cancer. For example, the extent of expression of biomarkers described herein may be used to determine the extent of progression of non-small lung cancer, the presence of pre-cancerous lesions, or staging of non-small lung cancer.

The invention also provides methods of diagnosing reactive airway disease and in particular diseases associated with over reactive $TH_2$ and $TH_{17}$ cells. Reactive airway diseases include asthma, chronic obstructive pulmonary disease, allergic rhinitis, cystic fibrosis, bronchitis, or other diseases manifesting hyper-reactivity to various physiological and/or environmental stimuli. In particular, the invention provides for methods of diagnosing asthma and chronic obstructive pulmonary disease, more particularly diagnosing asthma.

In particular embodiments, the subject is selected from those individuals who exhibit one or more symptoms of non-small cell lung cancer or reactive airway disease. Symptoms may include cough, shortness of breath, wheezing, chest pain, and hemoptysis; shoulder pain that travels down the outside of the arm or paralysis of the vocal cords leading to hoarseness; invasion of the esophagus may lead to difficulty swallowing. If a large airway is obstructed, collapse of a portion of the lung may occur and cause infections leading to abscesses or pneumonia. Metastases to the bones may produce excruciating pain. Metastases to the brain may cause neurologic symptoms including blurred vision headaches, seizures, or symptoms commonly associated with stroke such as weakness or loss of sensation in parts of the body. Lung cancers often produce symptoms that result from production of hormone-like substances by the tumor cells. A common paraneoplastic syndrome seen in NSCLC is the production parathyroid hormone like substances which cause calcium in the bloodstream to be elevated. Asthma typically produces symptoms such as coughing, especially at night, wheezing, shortness of breath and feelings of chest tightness, pain or pressure. Thus, it is apparent that many of the symptoms of asthma are common to NSCLC.

Methods of Diagnosing Non-Small Cell Lung Cancer

The invention provides for a method of diagnosing non-small cell lung cancer in a subject comprising, (a) obtaining a physiological sample of the subject; and (b) determining the extent of expression in said subject of at least one biomarker from Table 2, wherein the extent of expression of said at least one biomarker is indicative of the presence or development of non-small cell lung cancer.

In a preferred embodiment, the invention provides for methods of diagnosing non-small cell lung cancer in a subject comprising determining the extent of expression of a plurality of biomarkers from Table 2 in a physiological sample of the subject, wherein a pattern of expression of the plurality of markers are indicative of non-small cell lung cancer or correlate to a changes in a non-small cell lung cancer disease state (e.g., stages). In another preferred embodiment, patterns of expression correlate to an increased likelihood that a subject has or may have non-small cell lung cancer. Patterns of expression may be characterized by any technique known in the art for pattern recognition. The plurality of biomarkers may comprise any of the combinations of biomarkers described above with respect to Table 2.

In one embodiment, the subject is at-risk for non-small cell lung cancer. In one embodiment, levels of particular biomarkers associated with non-small cell cancer are determined for an individual, and levels which differ from those expected for the normal population suggest that the individual is "at-risk." In another embodiment, the number of relevant biomarkers from Table 2 which deviate statistically from normal is determined, with a greater number of deviant markers indicating greater risk of non-small cell cancer. In another embodiment, the subject is selected from those individuals who exhibit one or more symptoms of non-small cell lung cancer.

Methods of Diagnosing Reactive Airway Disease

The invention provides for a method of diagnosing reactive airway disease in a subject comprising, (a) obtaining a physiological sample of the subject; and (b) determining the extent of expression in said subject of at least one biomarker from Table 3, wherein the extent of expression of said at least one biomarker is indicative of reactive airway disease.

In a preferred embodiment, the invention provides for methods of diagnosing reactive airway disease in a subject comprising determining the extent of expression of a plurality of biomarkers from Table 3 in a physiological sample of the subject, wherein a pattern of expression of the plurality of markers are indicative of reactive airway disease or correlate to changes in a reactive airway disease state. In another preferred embodiment, patterns of expression correlate to an increased likelihood that a subject has or may have reactive airway disease. Patterns of expression may be characterized by any technique known in the art for pattern recognition. The plurality of biomarkers may comprise any of the combinations of biomarkers described above with respect to Table 3.

In one embodiment, the subject is at-risk for reactive airway disease. In one embodiment, levels of particular biomarkers associated with reactive airway disease are determined for an individual, and levels which differ from those expected for the normal population suggest that the individual is "at-risk." In another embodiment, the number of relevant biomarkers from Table 3 which deviate statistically from normal is determined, with a greater number of deviant markers indicating greater risk of reactive airway disease. In another embodiment, the subject is selected from those individuals who exhibit one or more symptoms of reactive airway disease.

Methods of Discriminating Between Non-Small Cell Lung Cancer and Reactive Airway Disease The invention also provides for a method of diagnosing a lung disease in a subject comprising, (a) obtaining a physiological sample of the subject; and (b) determining the extent of expression in said subject of at least one biomarker from Table 4, and preferably also at least one biomarker from Table 3, and at least one biomarker from Table 2, wherein (i) said at least one biomarker from each of Table 2, Table 3, and Table 4 is not identical, (ii) the extent of expression of said at least one biomarker from Table 2 and Table 3 is indicative of the lung disease of non-small cell lung cancer and reactive airway disease, respectively; and (iii) the extent of expression of said at least one biomarker from Table 4 assists in discriminating between the indication of non-small cell lung cancer and reactive airway disease.

In a preferred embodiment, the method comprises determining the extent of expression of a plurality of biomarkers from Table 4, and preferably also a plurality of biomarkers from Table 2, and a plurality of biomarkers from Table 4. In another preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described above with respect to Table 2, Table 3, and Table 4.

In one embodiment, the subject is at-risk for non-small cell lung cancer or reactive airway disease. In another embodiment, the subject is selected from those individuals who exhibit one or more symptoms of non-small lung cancer or reactive airway disease.

The invention also contemplates methods comprising determining the extent of expression in said subject of at least one biomarker listed in Table 2, Table 3, and Table 4. A biomarker listed in Table 2, Table 3, and Table 4 will assist in each of the determinations represented the Tables. The invention also contemplates methods comprising determining the extent of expression in said subject of at least 2, 3, 4, 5, 6, 7, 8, 9, 10, 11, 12, 13, 14, 15, 16, or 17 biomarkers listed in each of Table 2, Table 3, and Table 4.

The invention also provides a diagnostic method to assist in differentiating the likelihood that a subject is at-risk of developing or suffering from non-small cell lung cancer or reactive airway disease comprising, (a) obtaining a physiological sample of the subject who is at-risk for non-small cell lung cancer or reactive airway disease; and (b) determining the extent of expression in said subject of at least one biomarker from Table 4, wherein the extent of expression of said at least one biomarker from Table 4 assists in differentiating the likelihood that said subject is at risk of non-small cell lung cancer or reactive airway disease.

In a preferred embodiment, the method comprises determining the extent of expression of a plurality of biomarkers from Table 4. In another preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described above with respect to Table 4.

In one embodiment, the subject is selected from those individuals who exhibit one or more symptoms of non-small lung cancer or reactive airway disease. Methods of relating to "at-risk" subjects are described above and methods related thereto are contemplated herein.

Methods of Monitoring Therapy

The invention also provides a method of monitoring a subject comprising (a) determining a first extent of expression in said subject of at least one biomarker from Table 1 in a sample obtained from the subject; (b) determining a second extent of expression in said subject of said at least one biomarker from Table 1 using a second sample obtained from the subject at a different time than said first extent of expression; and (d) comparing said first extent of expression and said second extent of expression. Typically, the subject has experienced therapeutic intervention between the time the first and second samples were obtained. This embodiment is also useful to identify particular biomarkers which exhibit changes in their extent of expression in response to particular therapeutic interventions.

In a preferred embodiment, the method comprises determining the extent of expression of a plurality of biomarkers from Table 1. The plurality of biomarkers may comprise any of the combinations of biomarkers described above with respect to Table 1.

The embodiments described above refer to the biomarkers of Table 1. It will be appreciated, however, that the biomarkers of Table 2, Table 3, or Table 4 may be substituted for the biomarkers of Table 1 in any of the described embodiments.

Methods of Predicting a Subject's Response to Therapeutic Intervention

The invention also provides a method for predicting a subject's response to therapeutic intervention comprising, (a) obtaining a physiological sample of the subject; and (b) determining the extent of expression in said subject of at least one biomarker from Table 1, wherein the extent of expression of said at least one biomarker from Table 1 assists in predicting a subject's response to said therapeutic intervention. Preferred biomarkers for use in this embodiment are those biomarkers shown to be responsive to the therapeutic intervention of interested by monitoring a population of subjects. This embodiment may also be used for selection of those patients more likely to be responsive to therapy.

In a preferred embodiment, the method comprises determining the extent of expression of a plurality of biomarkers from Table 1. The plurality of biomarkers may comprise any of the combinations of biomarkers described above with respect to Table 1.

The embodiments described above refer to the biomarkers of Table 1. It will be appreciated, however, that the biomarkers of Table 2, Table 3, or Table 4 may be substituted for the biomarkers of Table 1 in any of the described embodiments.

Kits

The invention also provides a kit comprising, (a) first means for determining the extent of expression of at least one biomarker from Table 2; (b) second means for determining the extent of expression of at least one biomarker from Table 3; and (c) third means for determining the extent of expression of at least one biomarker from Table 4, wherein said at least one biomarker from Table 2, Table 3, and Table 4 are not identical.

In another embodiment, the kits comprise means for determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 biomarkers from Table 2, any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 biomarkers from Table 3, and any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 biomarkers from Table 4, wherein said biomarkers are not identical. In another embodiment, the kits comprise means for determining the extent of expression of any 2, 3, 4, 5, 6, 7, 8, 9, 10, 11, 12, 3, 14, 15, 16, 17, 18, or 19 biomarkers from biomarker nos. 1-20 of Table 2, any 2, 3, 4, 5, 6, 7, 8, 9, 10, 11, 12, 3, 14, 15, 16, 17, 18, or 19 biomarkers from biomarker nos. 1-20 of Table 3, and any 2, 3, 4, 5, 6, 7, 8, 9, 10, 11, 12, 3, 14, 15, 16, 17, 18, or 19 biomarkers from biomarker nos. 1-20 of Table 4, wherein said biomarkers are not identical. In another embodiment, the kits comprise means for determining the extent of expression of any 2, 3, 4, 5, 6, 7, 8, or 9 biomarkers from biomarker nos. 1-10 of Table 2, any 2, 3, 4, 5, 6, 7, 8, or 9 biomarkers from biomarker nos. 1-10 of Table 3, and any 2, 3, 4, 5, 6, 7, 8, or 9 biomarkers from biomarker nos. 1-10 of Table 4, wherein said biomarkers are not identical. In another embodiment, the kits comprise means for determining the extent of expression of any 2, 3, 4, or 5 biomarkers from biomarker nos. 1-6 of Table 2, any 2, 3, 4, or 5 biomarkers from biomarker nos. 1-6 of Table 3, and any 2, 3, 4, or 5 biomarkers from biomarker nos. 1-6 of Table 4, wherein said biomarkers are not identical. The invention contemplates that in any of the above embodiments the extent of expression of no more than 5, 10, 15, 20, 25, or 30 biomarkers are determined.

The invention also provides a kit comprising, (a) detection agents for detecting at least one biomarker from Table 2; (b) detection agents for detecting at least one biomarker from Table 3; and (c) detection agents for detecting at least one biomarker from Table 4, wherein said at least one biomarker from Table 2, Table 3, and Table 4 are not identical.

In another embodiment, the kits comprise detection agents for detecting any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 biomarkers from Table 2, any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 biomarkers from Table 3, and any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 biomarkers from Table 4, wherein said biomarkers are not identical. In another embodiment, the kits comprise detection agents for detecting any 2, 3, 4, 5, 6, 7, 8, 9, 10, 11, 12, 3, 14, 15, 16, 17, 18, or 19 biomarkers from biomarker nos. 1-20 of Table 2, any 2, 3, 4, 5, 6, 7, 8, 9, 10, 11, 12, 3, 14, 15, 16, 17, 18, or 19 biomarkers from biomarker nos. 1-20 of Table 3, and any 2, 3, 4, 5, 6, 7, 8, 9, 10, 11, 12, 3, 14, 15, 16, 17, 18, or 19 biomarkers from biomarker nos. 1-20 of Table 4, wherein said biomarkers are not identical. In another embodiment, the kits comprise detection agents for detecting any 2, 3, 4, 5, 6, 7, 8, or 9 biomarkers from biomarker nos. 1-10 of Table 2, any 2, 3, 4, 5, 6, 7, 8, or 9 biomarkers from biomarker nos. 1-10 of Table 3, and any 2, 3, 4, 5, 6, 7, 8, or 9 biomarkers from biomarker nos. 1-10 of Table 4, wherein said biomarkers are not identical. In another embodiment, the kits comprise detection agents for detecting any 2, 3, 4, or 5 biomarkers from biomarker nos. 1-6 of Table 2, any 2, 3, 4, or 5 biomarkers from biomarker nos. 1-6 of Table 3, and any 2, 3, 4, or 5 biomarkers from biomarker nos. 1-6 of Table 4, wherein said biomarkers are not identical. The invention contemplates that in any of the above embodiments no more than 5, 10, 15, 20, 25, or 30 biomarkers are detected.

The invention also provides a kit comprising means for determining the extent of expression of at least one polypeptide selected from the group consisting of SEQ ID NOS: 1-11. In one embodiment, the kit comprises means for determining the extent of expression of any combination of SEQ ID NOS: 1-11.

The invention also provides a kit comprising, detection agents for detecting at least one polypeptide selected from the group consisting of SEQ ID NOS: 1-11. In one embodiment, the kit comprises detection agents for detecting any combination of SEQ ID NOS: 1-11.

The invention also provides a kit comprising means for determining the extent of expression of at least one polypeptide selected from the group consisting of SEQ ID NOS: 1-11 and means for determining the extent of expression of at least one biomarker from Table 1.

In one embodiment, the kit comprises means for determining the extent of expression of at least one polypeptide selected from the group consisting of SEQ ID NOS: 1-11 and means for determining the extent of expression of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 biomarkers from Table 1. In another embodiment, the kit comprises means for determining the extent of expression of at least one polypeptide selected from the group consisting of SEQ ID NOS: 1-11 and means for determining the extent of expression of any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 biomarkers from Table 1. In another embodiment, the kit comprises means for determining the extent of expression of at least one polypeptide selected from the group consisting of SEQ ID NOS: 1-11, and means for determining the extent of expression of any 2, 3, 4, 5, 6, 7, 8, 9, 10, 11, 12, 3, 14, 15, 16, 17, 18, or 19 biomarkers from biomarker nos. 1-20 of Table 1. In another embodiment, the kit comprises means for determining the extent of expression of at least one polypeptide selected from the group consisting of SEQ ID NOS: 1-11, and means for determining the extent of expression of any 2, 3, 4, 5, 6, 7, 8, or 9 biomarkers from biomarker nos. 1-10 of Table 1. In another embodiment, the kit comprises means for determining the extent of expression of at least one polypeptide selected from the group consisting of SEQ ID NOS: 1-11, and means for determining the extent of expression of any 2, 3, 4, or 5 biomarkers from biomarker nos. 1-6 of Table 1. In another embodiment, the kit comprises means for determining the extent of expression of any combination of SEQ ID NOS: 1-11, and means for determining the extent of expression of any combination of biomarkers from Table 1 described above. The invention contemplates that in any of the above embodiments the extent of expression of no more than 2, 3, 4, 5, 10, 15, 20, 25, 30, 35, 40, 45, 50, or 54 biomarkers are determined.

The invention also provides a kit comprising, detection agents for detecting at least one polypeptide selected from the group consisting of SEQ ID NOS: 1-11, and detection agents for detecting at least one biomarker from Table 1.

In one embodiment, the kit comprises detection agents for detecting at least one polypeptide selected from the group consisting of SEQ ID NOS: 1-11, and detection agents for detecting any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 biomarkers from Table 1. In another embodiment, the kit comprises a detection agents for detecting at least one polypeptide selected from the group consisting of SEQ ID NOS: 1-11, and detection agents for detecting any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 biomarkers from Table 1. In another embodiment, the kit comprises detection agents for detecting at least one polypeptide selected from the group consisting of SEQ ID NOS: 1-11, and detection agents for detecting any 2, 3, 4, 5, 6, 7, 8, 9, 10, 11, 12, 3, 14, 15, 16, 17, 18, or 19 biomarkers from biomarker nos. 1-20 of Table 1. In another embodiment, the kit comprises detection agents for detecting at least one polypeptide selected from the group consisting of SEQ ID NOS: 1-11, and detection agents for detecting any 2, 3, 4, 5, 6, 7, 8, or 9 biomarkers from biomarker nos. 1-10 of Table 1. In another embodiment, the kit comprises detection agents for detecting at least one polypeptide selected from the group consisting of SEQ ID NOS: 1-11, and detection agents for detecting any 2, 3, 4, or 5 biomarkers from biomarker nos. 1-6 of Table 1. In another embodiment, the kit comprises detection agents for detecting any combination of SEQ ID NOS: 1-11, and detection agents for detecting any combination of biomarkers from Table 1 described above. The invention contemplates that in any of the above embodiments no more than 2, 3, 4, 5, 10, 15, 20, 25, 30, 35, 40, 45, 50, or 54 biomarkers are detected.

The following examples are not intended to limit the invention in any way.

Example 1

Human blood samples were collected from volunteers. Thirty samples were collected from individuals known not to have either non-small cell lung cancer or asthma. These thirty samples comprise, and are referred to herein as, the "normal population." Twenty-eight blood samples were collected from individuals known to have asthma and diagnosed as such by a physician. These twenty-eight samples comprise, and are referred to herein as, the "asthma population." Thirty blood samples were collected from individuals known to have non-small cell lung cancers and diagnosed as such by a physician. These thirty samples comprise, and are referred to herein as the "lung cancer population."

Research was performed to select biomarkers for which it was believed that altered expression levels would be associated with lung cancer or asthma. As used herein, "lung cancer" is meant to encompass those lung cancers which are known to be non-small celled lung cancers. The following fifty-nine biomarkers were selected to be tested: CD40, Hepatocyte Growth Factor ("HGF"), I-TAC, Leptin, Matrix Metalloproteinase ("MMP") 1, MMP 2, MMP3, MMP 7, MMP 8, MMP 9, MMP 12, MMP 13, CD40 Soluble Ligand ("CD40 Ligand"), Epidermal Growth Factor ("EFG"), Eotaxin, Fractalkine, Granulocyte Colony Stimulating Factor ("G-CSF"), Granulocyte Macrophage Colony Stimulating Factor ("GM-CSF"), Interferon γ ("IFN γ"), Interleukin ("IL") 1α, IL-1β, IL-1ra, IL-2, IL-4, IL-5, IL-6, IL-7, IL-8, IL-10, IL-12(p40), IL-12(p70), IL-13, IL-15, IL-17, IP-10, Monocyte Chemotactic Protein 1 ("MCP-1"), Macrophage Inflammatory Protein ("MIP") 1α, MIP-1β, Transforming Growth Factor α ("TGF α"), Tumor Necrosis Factor α ("TNF α"), Vascular Endothelial Growth Factor ("VEGF"), Insulin, C-peptide, Glucagon Like Protein-1/amyline ("GLP-1/amylin"), Amylin (total), Glucagon, Adiponectin, Plasminogen Activator Inhibitor 1 ("PAI-1") (active/total), Resistin, sFas, sFasL, Macrophage Migration Inhibitory Factor ("MIF"), sE-Selectin, Soluble Vascular Cell Adhesion Molecule ("sVCAM"), Soluble Intracellular Adhesion Molecule ("sICAM"), Myeloperoxidase ("MPO"), C-Reactive Protein ("CRP"), Serum Amyloid A ("SAA"), and Serum Amyloid P ("SAP").

Plasma specimens for each of the normal, asthma and lung cancer populations were screened for each of the fifty-nine biomarkers by subjecting the plasma specimens to analysis using Luminex's xMAP technology, a quantitative multiplexed immunoassay using automated bead-based technologies.

Eight different assay kits were used with the Luminex xMAP technology to screen the biomarkers, namely Millipore's Human Cytokine/Chemokine (Cat# MPXHCYTO-60K, Human Endocrine (Cat# HENDO-65K), Human Serum Adipokines (Cat# HADKI-61K), Human Sepsis/Apoptosis (Cat# HSEP-63K), Human Cardiovascular Panel 1 (Cat# HCVD1-67AK) and Human Cardiovascular Panel 2 (11CVD2-67BK) along with R&D Systems, Inc.'s Human Fluorokine MAP Profiling Base Kit B (Cat# LUB00) and Human Fluorokine MAP MMP Profiling Base Kit (Cat# LMP000). The fluorescence intensity levels resulting from the multiplexed immunoassay were recorded for each of the fifty-nine biomarkers for each plasma specimen for each population. The recorded fluorescence intensity is proportional to the concentration of the corresponding biomarker in the sample, and to the extent of its expression in the individual. Averages, standard deviations, and relative standard deviations for fluorescence intensity level associated with each biomarker for each population were calculated. FIGS. 1A through 1C show the average mean, standard deviation and relative standard deviation for each biomarker in the normal (NO), non-small lung cancer (LC), and asthma (AST) populations.

Student's t test was then used to characterize inter-pathology differences for each particular biomarker between each population. Mean fluorescence intensity measurements of each biomarker for the samples from normal patients were compared to those of the samples from patients suffering from lung cancer and also to those of samples derived from patients suffering from asthma. FIG. 1D shows the differences between the various population means for each marker. In addition, the mean fluorescence intensity measurements for the lung cancer patients were compared to the mean fluorescence intensity measurements for the asthma patients, and the significance was evaluated using the Student's t statistic.

Further analysis of the statistical differences for each biomarker between the normal, asthma and lung cancer populations was performed. To characterize the difference in mean expression levels for each biomarker between the populations, Student's t values were calculated using the t-test function available in the Microsoft EXCEL software package. The EXCEL t-test function was used to calculate the probability associated with the Student's t value under an assumption of equal variance using a two-tailed distribution.

The significance of the difference in expression levels between the populations was determined on the criteria that any Student's t value with an associated probability smaller than 0.05 was considered to be significant to indicate the presence of the given pathology, whether asthma or lung cancer. Using a criterion of 0.05 is generally accepted in the scientific community. Any Student's t value with an associated probability larger than 0.1 was considered to be insignificant to indicate the presence of the given pathology. Furthermore, any Student's t value with an associated probability between 0.05 and 0.1 was determined to be marginal. However, further experimentation and testing has been done for the biomarkers with Student's t values with an associated probability of 0.05 to 0.1 between the populations to verify their significance.

Referring now to FIG. 1E, the Student's t values with an associated probability calculated comparing each biomarker for each population is shown. It should be noted that the Student's t values with an associated probability shown in FIG. 1E are calculated on the basis that each of the asthma, normal, and lung cancer populations has a single mean and a normal distribution.

The significance of the differences in biomarker expression levels were used to rank the relative importance of the biomarkers. Those biomarkers that were found to be most significantly different between pathologies were classed as relatively more important. The measurements of mean fluorescence intensity were examined, and data for all biomarkers having intensities that did not depart significantly from the average intensities of specimens in the other populations were excluded from further analysis. Those biomarkers having relatively low relative standard deviation were classed as more significant than those having relatively high standard deviation.

The direction of deviation, i.e. whether the average level of a particular marker increased or decreased in any pathology relative to any of the other pathologies, was not used to judge the relative significance of a particular marker. In this way, a group of biomarkers was assembled that showed high variability between pathologies, relatively low relative standard deviation and good instrumental detectability (defined as non-zero uncorrected mean fluorescence intensity). Those calculations were used to test the efficiency of the immunoassay and analyzed to determine the biomarkers which showed significant differences in expression levels between the expression levels of the normal population, as well as to determine reference ranges which are characteristic of and associated with the pathologies of lung cancer and/or asthma.

Still referring to FIG. 1E, the probabilities associated with the Student's t values were calculated to compare the asthma population to the normal population. Significant differences between the asthma population and the normal population were determined from the Student's t probability for the biomarkers sE-Selectin, EGF, Leptin, IL-5, PAI-1, Resistin, MMP-13, CD40 Ligand sVCAM-1, HGF, C-Peptide, sICAM-1, MMP-7, Adiponectin, GM-CSF and MIF. This determination was made on the basis that, when comparing the twenty-eight specimens from the asthma population with the thirty specimens from the normal population using the Student's t function described herein, the probabilities associated with the Student's t value for each of these biomarkers was smaller than 0.05. Difference was determined to be insignificant between the asthma population and the normal population for the biomarkers CRP, MMP-9, IL-4, IL-1α, SAA, IL-7 and IL-6, as the Student's t probability for each of these was significantly greater than 0.05.

As also shown in FIG. 1E, the probabilities associated with the Student's t values were calculated to compare the lung cancer population to the normal population. Significant difference between the lung cancer population and the normal population was determined from the Student's t probability for the biomarkers sE-Selectin, EGF, Leptin, IL-5, PAI-1, Resistin, CRP, MMP-9, IL-4, IL-1α, SAA, IL-7, CD40 Ligand, MMP-7 and MMP-12. Again, this determination was made on the basis that, when comparing the thirty specimens from the lung cancer population with the thirty specimens from the normal population using the Student's t function described herein, the Student's t probability for each of these biomarkers was smaller than 0.05. Difference was determined to be insignificant between the lung cancer population and the normal population for the biomarkers MMP-13, HGF, C-Peptide, sICAM, Adiponectin, GM-CSF, IL-17, TNF α, ITAC and MIF, as the Student's t probability for each of these biomarkers was significantly greater than 0.05.

Three biomarkers had probabilities associated with the Student's t values only slightly greater than 0.05 between the lung cancer population and the normal population. Specifically, when comparing the lung cancer population to the normal population, IL-6 had a Student's t probability of 0.076195528, sVCAM-1 had a Student's t probability of 0.08869949, and IL-15 had a Student's T probability of 0.086324372. These biomarkers are regarded as having insignificant difference between the lung cancer population and the normal population. However, due to the fact that the Student's t probability for these three biomarkers are close to 0.05, it is possible that each population may significantly vary between the normal and lung cancer populations.

Finally, as shown in FIG. 1E, further analysis was done by calculating the probabilities associated with the Student's t values to compare the lung cancer population to the asthma population. Significant difference between the lung cancer population and the asthma population was determined from the Student's t probability for the biomarkers sE-Selectin, EGF, Leptin, IL-5, PAI-1, Resistin, CRP, MMP-9, IL-4, IL-1α, SAA, IL-7, IL-6, MMP-13 sVCAM, HGF, C-Peptide, sICAM, Adiponectin, GM-CSF, IL-17, IL-15, TNF α and I-TAC. This determination was made on the basis that, when comparing the thirty specimens from the lung cancer population with the twenty-eight specimens from the asthma population using the Student's t function described herein, the Student's t probability for each of these biomarkers was smaller than 0.05. Difference was determined to be insignificant between the lung cancer population and the asthma population for the biomarkers CD40 Ligand, MMP-7, MMP-12 and MIF, as the Student's t probability for each of these biomarkers was significantly greater than 0.05.

Example 2

Human blood samples were collected from volunteers. One hundred forty-two samples were collected from individuals known not to have either non-small cell lung cancer or asthma. These samples comprise, and are referred to herein as, the "normal population." One hundred eight blood samples were collected from individuals known to have asthma and diagnosed as such by a physician. These samples comprise, and are referred to herein as, the "asthma population." One hundred forty-six blood samples were collected from individuals known to have non-small cell lung cancers and diagnosed as such by a physician. These comprise, and are referred to herein as the "lung cancer population."

The same methods described in Example 1 were performed. FIGS. 2A-2E show the results obtained. These results provide guidance for selecting suitable biomarkers for the methods of this invention. In particular, the probability values for particular markers are useful in this regard.

FIG. 2E shows the probability associated with the effectiveness of various biomarkers for discriminating between the physiological state of different populations. Probability values of 0.1 or less are highlighted on this table to identify biomarkers of interest. Biomarkers used in preferred methods of this invention will have probability values of 0.05 or less, more preferably 0.01, and even more preferably 0.001 or less.

Example 3

Human blood samples were collected from volunteers. Thirty samples were collected from individuals known not to have either non-small cell lung cancer or asthma. The individuals known not to have either non-small cell lung cancer or asthma comprise, and are referred to herein as, the "normal population." Twenty-eight blood samples were collected from individuals known to have asthma and diagnosed as such by a physician. The individuals known to have asthma comprise, and are referred to herein as, the "asthma population." Thirty blood samples were collected from individuals known to have non-small cell lung cancers and diagnosed as such by a physician. The individuals known to have non-small cell lung cancer comprise, and are referred to herein as the "lung cancer population." Generally, as used herein, the term "lung cancer" or "lung cancers" is meant to refer to non-small cell lung cancers.

Eight to ten plasma specimens from each of the asthma population, normal population and lung cancer population were selected at random to be tested. Each plasma specimen from each population was subjected to a protease or digesting agent. Trypsin was used as the protease, and is desirable to be used as a protease because of its ability to make highly specific and highly predictable cleavages due to the fact that trypsin is known to cleave peptide chains at the carboxyl side of the lysine and arginine, except where a proline is present immediately following either the lysine or arginine. Although trypsin was used, it is possible to use other proteases or digesting agents. It is desirable to use a protease, or mixture of proteases, which cleave at least as specifically as trypsin.

The tryptic peptides, which are the peptides left by the trypsin after cleavage, were then separated from the insoluble matter by subjecting the specimens to a centrifugation and a capillary liquid chromatography, with an aqueous acetonitrile gradient with 0.1% formic acid using a 0.375×180 mm Supelcosil ABZ+ column on an Eksigent 2D capillary HPLC to effect chromatographic resolution of the generated tryptic peptides. This separation of the peptides is necessary because the electrospray ionization process is subject to ion co-suppression, wherein ions of a type having a higher proton affinity will suppress ion formation of ions having lower proton affinities if they are simultaneously eluting from the electrospray emitter, which in this case is co-terminal with the end of the HPLC column.

This methodology allows for the chromatographic separation of the large number of peptides produced in the tryptic digestions and helps to minimize co-suppression problems, thereby maximizing chances of the formation of pseudo-molecular ion co-suppression, thereby maximizing ion sampling. The tryptic peptides for each specimen were then subjected to an LC-ESIMS. The LC-ESIMS separated each peptide in each specimen in time by passing the peptides in each specimen through a column of solvent system consisting of water, acetonitrile and formic acid as described above.

The peptides were then sprayed with an electrospray ionization source to ionize the peptides and produce the peptide pseudo-molecular ions as described above. The peptides were passed through a mass analyzer in the LC-ESIMS where molecular masses were measured for each peptide pseudo-molecular ion. After passing through the LC-ESIMS, mass spectral readouts were produced for the peptides present in each sample from the mass spectral data, namely the intensities, the molecular weights and the time of elution from a chromatographic column of the peptides. The mass spectral readouts are generally graphic illustrations of the peptide pseudo-molecular ion signals recorded by the LC-ESIMS, wherein the x-axis is the measurement of mass to charge ratio, the y-axis is the intensity of the pseudo-molecular ion signal. These data are then processed by a software system that controls the LC-ESIMS and acquires and stores the resultant data.

Once the mass spectral data was obtained and placed on the mass spectral readouts, a comparative analysis was performed wherein the mass spectral readouts of each plasma specimen tested in the LC-ESIMS for each population was performed, both interpathologically and intrapathalogically. The mass spectral peaks were compared between each specimen tested in the normal population. The mass spectral peaks were then compared between each specimen tested in the asthma population and the lung cancer population. Once the intrapathological comparisons were performed, interpathological comparisons were performed wherein the mass spectral readouts for each specimen tested in the LC-ESIMS for the asthma population was compared against each specimen tested in the normal population. Likewise, the mass spectral readouts for each specimen tested in the LC-ESIMS for the lung cancer population was compared against each specimen tested in the normal population.

Peptides with mass spectral readouts that indicated the peptide intensities were inconsistently differentially expressed intrapathologically or were not substantially altered (less than 10 fold variance in intensity) when comparing the asthma population or lung cancer population to the normal population were determined to be insignificant and excluded. Generally, the exclusion criteria used involved comparing the peptide peak intensities for at least half of the identified characteristic peptides for a given protein across at least ten data sets derived from the analysis of individual patient plasma specimens from each pathology. If the intensity of the majority of peptide peaks derived from given protein were at least 10 fold higher in intensity for 80% of the plasma data sets, the protein was classed as differentially regulated between the two pathologic classes.

However, the identity of the proteins giving rise to the peptides that were observed to be differentially regulated were unknown and needed to be identified. To make the identification of the proteins, peptide pseudo-molecular ion signal intensities were compared across known databases which contain libraries of known proteins and peptides and suspected proteins and peptides.

The mass spectral readouts of the tryptic digests for each specimen from each of the normal, lung cancer and asthma population were inputted into a known search engine called Mascot. Mascot is a search engine known in the art which uses mass spectrometry data to identify proteins from four major sequencing databases, namely the MSDB, NCBInr, SwissProt and dbEST databases. These databases contain information on all proteins of known sequence and all putative proteins based on observation of characteristic protein transcription initiation regions derived from gene sequences. These databases are continually checked for accuracy and redundancy and are subject to continuous addition as new protein and gene sequences are identified and published in the scientific and patent literature.

Search criteria and parameters were inputted into the Mascot program and the mass spectral data from the mass spectral readouts for each population were run through the Mascot program. The mass spectral data entered into the Mascot program were for the all specimens of each pathology. The Mascot program then ran the mass spectral data for the peptides inputted against the sequencing databases, comparing the peak intensities and masses of each peptide to the masses and peak intensities of known peptides and proteins. Mascot then produced a search result which returned a candidate list of possible protein identification matches, commonly known as "significant matches" for each sample that was analyzed.

Significant matches are determined by the Mascot program by assigning a score called a "Mowse score" for each specimen tested. The Mowse score is an algorithm wherein the score is $-10*LOG_{10}(P)$, where P is the probability that the observed match is a random event, which correlates into a significance p value where p is less than 0.05, which is the generally accepted standard in the scientific community. Mowse scores of approximately 55 to approximately 66 or greater are generally considered significant. The significance level varies somewhat due to specific search considerations and database parameters. The significant matches were returned for each peptide run, resulting in a candidate list of proteins.

Next, comparative analysis was performed comparing the mass spectral readouts for each specimen tested from the asthma population and the lung cancer population to each specimen tested from the normal population. Each tryptic peptide pseudo-molecular ion signal (peak) associated with an putatively identified protein that was detected in the LC-ESIMS was compared across asthma, lung cancer and normal pathologies. Peptides with mass spectral peak intensities that indicated the peptide quantities were not substantially altered when comparing the asthma population or lung cancer population to the normal population were determined to be insignificant and excluded. Generally, the exclusion criteria used involved comparing the peptide peak intensities for at least half of the identified characteristic peptides for a given protein across at least ten data sets derived from the analysis of individual patient plasma specimens from each pathology. If the intensity of the majority of peptide peaks derived from given protein were at least 10 fold higher in intensity for 80% of the plasma data sets, the protein was classed as differentially regulated between the two pathologic classes.

The data from the mass spectral readouts were cross checked with the significant matches to confirm the raw data, peak identities, charge multiplicities, isotope distribution and flanking charge states. A reverse search was then performed to add peptides to the candidate list which may have been missed by the automated search through the Mascot program. The additional peptides were identified by selecting the "best match" meaning the single protein which substantially matched each parameter of the peptide compared, performing an in silico digest wherein the tryptic peptides and their respective molecular masses calculated based on the known amino acid or gene sequence of the protein. These predicted peptide masses were then searched against the raw mass spectral data and any peaks identified were examined and qualified as described above. Then, all of the peptides including those automatically identified by Mascot and those identified by manual examination were entered into the mass list used by Mascot. The refined match is then used to derive a refined Mowse score.

As a result of the identification process, the eleven proteins determined to be significantly differentially expressed between the asthma population, lung cancer population and/or normal population were identified as BAC04615, Q6NSC8, CAF17350, Q6ZUD4, Q8N7P1, CAC69571, FERM domain containing protein 4, JCC1445 proteasome endopeptidase complex chain C2 long splice form, Syntaxin 11, AAK13083, and AAK130490. BAC04615, Q6NSC8, CAF 17350, Q6ZUD4, Q8N7P1 are identified proteins resulting from genetic sequencing efforts. FERM domain containing protein 4 is known to be involved in intracytoplasmic protein membrane anchorage. JCC1445 proteasome endopeptidase complex chain C2 long splice form is a known proteasome. Syntaxin 11 is active in cellular immune response. BAC04615, AAK13083, and AAK130490 are major histocompatibility complex ("MHC") associated proteins.

Having identified eleven specific proteins which are consistently differentially expressed in asthma and lung cancer patients, it is possible to diagnose these pathologies early in the progression of the diseases by subjecting proteins in a patient's plasma to tryptic digestion and analysis by the LC-ESIMS, obtaining the mass spectral data, and determining whether the mass spectral data includes peaks for one or more of BAC04615, Q6NSC8, CAF17350, Q6ZUD4, Q8N7P1, CAC69571, FERM domain containing protein 4, JCC1445 proteasome endopeptidase complex chain C2 long splice form, Syntaxin 11, AAK13083, and AAK130490. The levels of any proteins found in the patient sample are then compared to the levels found in a normal population.

The amino acid sequence disclosed in SEQ ID NO: 1 is the primary amino acid sequence known as of the date of filing this application for the protein BAC04615. The amino acid sequence disclosed in SEQ ID NO: 2 is the primary amino acid sequence known as of the date of filing this application for the protein Q6NSC8. The amino acid sequence disclosed in SEQ ID NO: 3 is the primary amino acid sequence known as of the date of filing this application for the protein CAF17350. The amino acid sequence disclosed in SEQ ID NO: 4 is the primary amino acid sequence known as of the date of filing this application for the protein Q6ZUD4. The amino acid sequence disclosed in SEQ ID NO: 5 is the primary amino acid sequence known as of the date of filing this application for the protein FERM domain containing protein 4. The amino acid sequence disclosed in SEQ ID NO: 6 is the primary amino acid sequence known as of the date of filing this application for the protein AAK13083. The amino acid sequence disclosed in SEQ ID NO: 7 is the primary amino acid sequence known as of the date of filing this application for the protein Q8N7P1. The amino acid sequence disclosed in SEQ ID NO: 8 is the primary amino acid sequence known as of the date of filing this application for the protein CAC69571. The amino acid sequence disclosed in SEQ ID NO: 9 is the primary amino acid sequence known as of the date of filing this application for the protein JCC1445 proteasome endopeptidase complex chain C2 long splice. The amino acid sequence disclosed in SEQ ID NO: 10 is the primary amino acid sequence known as of the date of filing this application for the protein Syntaxin 11. The amino acid sequence disclosed in SEQ ID NO: 11 is the primary amino acid sequence known as of the date of filing this application for the protein AAK13049.

Example 4

Diagnostic Test for Non-Small Cell Lung Cancer

A sample of a biological fluid is obtained from a patient for whom diagnostic information is desired. The sample is preferably blood serum or plasma. The concentration in the sample of seven (7) of the following 14 biomarkers is determined: Resistin, PAI-1, MPO, CRP, SAA, SAP, C-peptide, sFSI, IL-1 alpha, IL-5, IL-5, IL-8, Interferon gamma, and MCP-1. The measured concentration from the sample for each biomarker is compared to the range of concentrations of that marker found in the same fluid in normal human individuals, a population of individuals diagnosed with asthma, and a population of individuals diagnosed with NSCLC. Deviation from the normal range is indicative of lung disease, and deviation from the range for the population of individuals with asthma is indicative of NSCLC. Tests on a patient using biomarkers from the same set of 14 may be used in analogous procedures for diagnosis of asthma or other reactive airway diseases.

Example 5

Monitoring Therapy for Non-Small Cell Lung Cancer

A pretreatment sample of a biological fluid is obtained from a patient who has been diagnosed with NSCLS before any treatment for the disease. The sample is preferably blood serum or plasma. The concentration in the sample of eight (8) of the following 24 biomarkers is determined: Resistin, PAI-1, SE-selectin, sICAM-1, MPO, CRP, SAA, SAP, Leptin, Amylin, C-peptide, sFSI, MIF, IL-1 alpha, IL-1 beta, IL-1ra, IL-5, IL-5, IL-8, IL-12 (p40) free, IL-17, Interferon gamma, MIP-1 alpha and MCP-1. The measured concentration from the sample for each biomarker may be compared to the range of concentrations of that marker found in the same fluid in normal human individuals. After the pretreatment sample has been taken the patient undergoes therapeutic intervention comprising surgery followed by irradiation. Samples of the same fluid are taken after surgery, but before irradiation. Additional samples are taken after each irradiation session. The concentration in each sample of the same eight (8) biomarkers is determined. Changes in the level of expression of each biomarker are noted and compared with other symptoms of progression of the disease.

Example 6

Selection of Predictive Biomarkers

A pretreatment sample of a biological fluid is obtained from a population of patients who have been diagnosed with NSCLS before any treatment for the disease. The sample is preferably blood serum or plasma. The concentration in the sample of the following 24 biomarkers is determined: Resistin, PAI-1, SE-selectin, sICAM-1, MPO, CRP, SAA, SAP, Leptin, Amylin, C-peptide, sFSI, MIF, IL-1 alpha, IL-1 beta, IL-1ra, IL-5, IL-5, IL-8, IL-12 (p40) free, IL-17, Interferon gamma, MIP-1 alpha and MCP-1. The measured concentration from the sample for each biomarker is compared to the range of concentrations of that marker found in the same fluid in normal human individuals. After the pretreatment sample has been taken each patient undergoes therapeutic intervention comprising surgery followed by irradiation. Samples of the same fluid are taken after surgery, but before irradiation. Additional samples are taken after each irradiation session. The concentration in each sample of the 24 biomarkers is determined. Changes in the level of expression of each biomarker are noted and compared with other symptoms of progression of the disease. All biomarkers whose level changes after therapy are identified.

Example 7

Selection of Susceptible Patients

A sample of a biological fluid is obtained from a patient who has been diagnosed with NSCLS. The sample is preferably blood serum or plasma. The concentration in the sample of each of the biomarkers identified in the previous example is determined, and patients for whom the highest number of biomarkers show values deviating from normal are selected for treatment.

The invention claimed is:

1. A method of physiological characterization in a subject comprising determining the extent of expression of at least three biomarkers from Table 1 in a physiological sample of said subject, wherein the extent of expression of said at least three biomarkers are indicative of a lung disease.

2. The method of claim 1, wherein said lung disease is reactive airway disease.

3. The method of claim 2, wherein said reactive airway disease is asthma.

4. The method of claim 1, wherein said method comprises determining the extent of expression of at least four biomarkers from Table 1 in a physiological sample of said subject.

5. The method of claim 4, wherein said biomarker is a polypeptide.

6. The method of claim 1, wherein the physiological sample is biological fluid.

7. The method of claim 6, wherein the biological fluid is blood serum or plasma.

8. The method of claim 1, wherein the subject is a mammal.

9. The method of claim 8, wherein the mammal is a human.

10. The method of claim 1, wherein the method of determining the extent of expression comprises performing a quantitative multiplex immunoassay.

11. The method of claim 1, wherein said method comprises determining the extent of expression of at least five biomarkers from Table 1 in a physiological sample of said subject.

12. The method of claim 1, wherein said method comprises determining the extent of expression of at least six biomarkers from Table 1 in a physiological sample of said subject.

13. The method of claim 1, wherein said lung disease is non-small cell lung cancer.

14. The method of claim 4, wherein said lung disease is non-small cell lung cancer.

15. The method of claim 11, wherein said lung disease is non-small cell lung cancer.

16. The method of claim 12, wherein said lung disease is non-small cell lung cancer.

17. The method of claim 4, wherein said lung disease is reactive airway disease.

18. The method of claim 17, wherein said reactive airway disease is asthma.

19. The method of claim 11, wherein said lung disease is reactive airway disease.

20. The method of claim 19, wherein said reactive airway disease is asthma.

21. The method of claim 12, wherein said lung disease is reactive airway disease.

22. The method of claim 21, wherein said reactive airway disease is asthma.

23. The method of claim 1, wherein the subject exhibits one or more symptoms of non-small cell lung cancer or reactive airway disease.

24. The method of claim 4, wherein the subject exhibits one or more symptoms of non-small cell lung cancer or reactive airway disease.

25. The method of claim 1, wherein the biomarkers comprise MIF; Leptin; IL-8; IL-12 (p40), free; or combinations thereof.

26. The method of claim 4, wherein the biomarkers comprise MIF; Leptin; IL-8; and IL-12 (p40), free.

27. The method of claim 23, wherein the biomarkers comprise MIF; Leptin; IL-8; IL-12 (p40), free; or combinations thereof.

28. The method of claim 24, wherein the biomarkers comprise MIF; Leptin; IL-8; and IL-12 (p40), free.

\* \* \* \* \*